(12) United States Patent
Baek

(10) Patent No.: US 9,783,575 B2
(45) Date of Patent: Oct. 10, 2017

(54) METHYL DEGRON PEPTIDE AND METHODS OF CONTROLLING PROTEIN LIFESPAN

(71) Applicant: Seoul National University (SNU) R&D Foundation, Seoul (KR)

(72) Inventor: Sung Hee Baek, Seoul (KR)

(73) Assignee: SNU R&D FOUNDATION, Seoul (KR)

( * ) Notice: Subject to any disclaimer, the term of this patent is extended or adjusted under 35 U.S.C. 154(b) by 0 days.

(21) Appl. No.: 14/051,547

(22) Filed: Oct. 11, 2013

(65) Prior Publication Data
US 2015/0105326 A1    Apr. 16, 2015

(30) Foreign Application Priority Data

Oct. 11, 2012  (KR) .................. 10-2012-0112712

(51) Int. Cl.
*C07K 7/08* (2006.01)
*C07K 14/705* (2006.01)

(52) U.S. Cl.
CPC .......... *C07K 7/08* (2013.01); *C07K 14/70567* (2013.01); *C07K 2319/31* (2013.01); *C07K 2319/90* (2013.01); *C07K 2319/95* (2013.01)

(58) Field of Classification Search
None
See application file for complete search history.

(56) References Cited

U.S. PATENT DOCUMENTS 5,763,212 A * 6/1998 Varshavsky ............ C07K 14/00
435/252.3

OTHER PUBLICATIONS

Yanzhong Yang and Mark T. Bedford, "Titivated for Destruction: the methyl-degron," Mol Cell. Nov. 30, 2012; 48(4): 487-488.*
Lee, et al, "EZH2 Generates a Methyl Degron that Is Recognized by the DCAF1/DDB1/CUL4 E3 Ubiquitin Ligase Complex," Molecular Cell, vol. 48, Issue 4, Nov. 30, 2012, pp. 572-586.*

* cited by examiner

*Primary Examiner* — Thomas S Heard
(74) *Attorney, Agent, or Firm* — The PL Law Group, PLLC

(57) ABSTRACT

The present invention provides an isolated methyl degron peptide and a fusion protein comprising a methyl degron peptide. Also, the present invention provides screening methods for agents affecting protein lifespan and anti-cancer agents. Moreover, the present invention provides methods of controlling protein lifespan, regulating protein expression, and treating cancers by using a methyl degron peptide or a methyl degron gene.

1 Claim, 50 Drawing Sheets

DCAF1 (VprBP)

HP1-chromo    EEETAVEKIIDRRVRKGKVEYYLKWKGYPETENTWEPENNLDC (SEQ ID NO: 22)
Pc-chromo     DLVTAAEKIIQKRVKKGVVEYRVKWKGWNQRYNTWEPEVNILD (SEQ ID NO: 23)
MRG15-chromo  ---YEAK-CVKVAIKDKQVKYFIHYSGWNKNWDEWVPESRVLK (SEQ ID NO: 24)
DCAF1-chromo  ---SYTHEQIVEM------MEFLIEY-GPAQLY--WEPAEVELK (SEQ ID NO: 25)

FIG. 39

```
HP1-chromo            EEEYAVEKIIDRRVRKGKVEYYLKWKGYPETENTWEPENNLDC   (SEQ ID NO: 22)
Pc-chromo             DLVYAAEKIIQKRVKKGVVEYRVKWKGWNQRYNTWEPEVNILD   (SEQ ID NO: 23)
DCAF1-chromo          --SYTHEQIVEM------MEFLIEY--GPAQLY--WEPAEVFLK   (SEQ ID NO: 25)
DCAF1-chromo-modified --SYTHEQIVEM------MEFLIEYKGPAQLYNTWEPAEVFLK   (SEQ ID NO: 26)
```

RORα/H3 chimeric protein

H3: KQLATKAARKSAPATGGVK (SEQ ID NO: 27)

SEQUENCE LISTING

<160> NUMBER OF SEQ ID NOS: 28

<210> SEQ ID NO 1
<211> LENGTH: 14
<212> TYPE: PRT
<213> ORGANISM: Artificial Sequence
<220> FEATURE:
<223> OTHER INFORMATION: Methyl Degron

<400> SEQUENCE: 1

Pro Leu Asn Gln Glu Ser Ala Arg Lys Ser Glu Pro Pro Ala
1               5                   10

<210> SEQ ID NO 2
<211> LENGTH: 42
<212> TYPE: DNA
<213> ORGANISM: Artificial Sequence
<220> FEATURE:
<223> OTHER INFORMATION: Methyl Degron

<400> SEQUENCE: 2
ccgctgaacc aggaatccgc cgcaagagc gagccgcctg cc                              42

<210> SEQ ID NO 3
<211> LENGTH: 10
<212> TYPE: PRT
<213> ORGANISM: Artificial Sequence
<220> FEATURE:
<223> OTHER INFORMATION: partial ROR-alpha

<400> SEQUENCE: 3

Leu Asn Gln Glu Ser Ala Arg Lys Ser Glu
1               5                   10

<210> SEQ ID NO 4
<211> LENGTH: 15
<212> TYPE: PRT
<213> ORGANISM: Artificial Sequence
<220> FEATURE:
<223> OTHER INFORMATION: partial H3K27

<400> SEQUENCE: 4

Gln Leu Ala Thr Lys Ala Ala Arg Lys Ser Ala Pro Ala Thr Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: hRORalpha

<400> SEQUENCE: 5

Pro Leu Asn Gln Glu Ser Ala Arg Lys Ser Glu Pro Pro Ala Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: mRORalpha

<400> SEQUENCE: 6

Pro Leu Thr Gln Asp Thr Gly Arg Lys Ser Glu Ala Pro Gly Ala
1               5                   10                  15

```
<210> SEQ ID NO 7
<211> LENGTH: 14
<212> TYPE: PRT
<213> ORGANISM: Artificial Sequence
<220> FEATURE:
<223> OTHER INFORMATION: DCAF1

<400> SEQUENCE: 7

Gly Asp Ile Ala His Ile Tyr Asp Ile Gln Thr Gly Asn Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: DCAF1

<400> SEQUENCE: 8

Ile Ser Phe Pro Glu Lys Glu Leu Leu Leu Ile Arg
1               5                   10

<210> SEQ ID NO 9
<211> LENGTH: 16
<212> TYPE: PRT
<213> ORGANISM: Artificial Sequence
<220> FEATURE:
<223> OTHER INFORMATION: DCAF1

<400> SEQUENCE: 9

Val Ser Gly Lys Pro Leu Leu Ile Gly Thr Asp Val Ser Leu Ala Arg
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: DCAF1

<400> SEQUENCE: 10

Leu Leu Thr Leu Phe Asn Pro Asp Leu Ala Asn Asn Tyr Lys Arg
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: DCAF1

<400> SEQUENCE: 11

His Leu Pro Ser Pro Pro Thr Leu Asp Ser Ile Ile Thr Glu Tyr Leu
1               5                   10                  15

Arg

<210> SEQ ID NO 12
<211> LENGTH: 9
<212> TYPE: PRT
<213> ORGANISM: Artificial Sequence
<220> FEATURE:
<223> OTHER INFORMATION: DDB1

<400> SEQUENCE: 12

Asp Leu Leu Phe Ile Leu Thr Ala Lys
1               5
```

<210> SEQ ID NO 13
<211> LENGTH: 9
<212> TYPE: PRT
<213> ORGANISM: Artificial Sequence
<220> FEATURE:
<223> OTHER INFORMATION: DDB1

<400> SEQUENCE: 13

Tyr Leu Leu Gly Asp Met Glu Gly Arg
1               5

<210> SEQ ID NO 14
<211> LENGTH: 10
<212> TYPE: PRT
<213> ORGANISM: Artificial Sequence
<220> FEATURE:
<223> OTHER INFORMATION: DDB1

<400> SEQUENCE: 14

Glu Met Leu Gly Gly Glu Ile Ile Pro Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: DDB1

<400> SEQUENCE: 15

Ile Val Val Phe Gln Tyr Ser Asp Gly Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: DDB1

<400> SEQUENCE: 16

Ala Leu Val Ser Glu Trp Lys Glu Pro Gln Ala Lys
1               5                   10

<210> SEQ ID NO 17
<211> LENGTH: 15
<212> TYPE: PRT
<213> ORGANISM: Artificial Sequence
<220> FEATURE:
<223> OTHER INFORMATION: DDB1

<400> SEQUENCE: 17

Glu Thr Asp Asp Thr Leu Val Leu Ser Phe Val Gly Gln Thr Arg
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: RORalpha

<400> SEQUENCE: 18

Ile Gln Leu Ala Leu Gln His Val Leu Gln Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: RORalpha

<400> SEQUENCE: 19

Lys Thr His Thr Ser Gln Ile Glu Ile Ile Pro Cys Lys
1               5                   10

<210> SEQ ID NO 20
<211> LENGTH: 18
<212> TYPE: PRT
<213> ORGANISM: Artificial Sequence
<220> FEATURE:
<223> OTHER INFORMATION: RORalpha

<400> SEQUENCE: 20

Arg Ile Asp Gly Phe Met Glu Leu Cys Gln Asn Asp Gln Ile Val Leu
1               5                   10                  15

Leu Lys

<210> SEQ ID NO 21
<211> LENGTH: 22
<212> TYPE: PRT
<213> ORGANISM: Artificial Sequence
<220> FEATURE:
<223> OTHER INFORMATION: RORalpha

<400> SEQUENCE: 21

Glu Glu Leu Gln Gln Ile Thr Trp Gln Thr Phe Leu Gln Glu Glu Ile
1               5                   10                  15

Glu Asn Tyr Gln Asn Lys
            20

<210> SEQ ID NO 22
<211> LENGTH: 43
<212> TYPE: PRT
<213> ORGANISM: Artificial Sequence
<220> FEATURE:
<223> OTHER INFORMATION: HP1-chromo

<400> SEQUENCE: 22

Glu Glu Glu Tyr Ala Val Glu Lys Ile Ile Asp Arg Arg Val Arg Lys
1               5                   10                  15

Gly Lys Val Glu Tyr Tyr Leu Lys Trp Lys Gly Tyr Pro Glu Thr Glu
            20                  25                  30

Asn Thr Trp Glu Pro Glu Asn Asn Leu Asp Cys
        35                  40

<210> SEQ ID NO 23
<211> LENGTH: 43
<212> TYPE: PRT
<213> ORGANISM: Artificial Sequence
<220> FEATURE:
<223> OTHER INFORMATION: Pc-chromo

<400> SEQUENCE: 23

Asp Leu Val Tyr Ala Ala Glu Lys Ile Ile Gln Lys Arg Val Lys Lys
1               5                   10                  15

Gly Val Val Glu Tyr Arg Val Lys Trp Lys Gly Trp Asn Gln Arg Tyr
            20                  25                  30

Asn Thr Trp Glu Pro Glu Val Asn Ile Leu Asp
                35                  40

<210> SEQ ID NO 24
<211> LENGTH: 39
<212> TYPE: PRT
<213> ORGANISM: Artificial Sequence
<220> FEATURE:
<223> OTHER INFORMATION: MRG15-chromo

<400> SEQUENCE: 24

Tyr Glu Ala Lys Cys Val Lys Val Ala Ile Lys Asp Lys Gln Val Lys
1               5                   10                  15

Tyr Phe Ile His Tyr Ser Gly Trp Asn Lys Asn Trp Asp Glu Trp Val
                20                  25                  30

Pro Glu Ser Arg Val Leu Lys
        35

<210> SEQ ID NO 25
<211> LENGTH: 32
<212> TYPE: PRT
<213> ORGANISM: Artificial Sequence
<220> FEATURE:
<223> OTHER INFORMATION: DCAF1-chromo

<400> SEQUENCE: 25

Ser Tyr Thr His Glu Gln Ile Val Glu Met Met Glu Phe Leu Ile Glu
1               5                   10                  15

Tyr Gly Pro Ala Gln Leu Tyr Trp Glu Pro Ala Glu Val Phe Leu Lys
                20                  25                  30

<210> SEQ ID NO 26
<211> LENGTH: 35
<212> TYPE: PRT
<213> ORGANISM: Artificial Sequence
<220> FEATURE:
<223> OTHER INFORMATION: DCAF1-chromo-modified

<400> SEQUENCE: 26

Ser Tyr Thr His Glu Gln Ile Val Glu Met Met Glu Phe Leu Ile Glu
1               5                   10                  15

Tyr Lys Gly Pro Ala Gln Leu Tyr Asn Thr Trp Glu Pro Ala Glu Val
                20                  25                  30

Phe Leu Lys
        35

<210> SEQ ID NO 27
<211> LENGTH: 19
<212> TYPE: PRT
<213> ORGANISM: Artificial Sequence
<220> FEATURE:
<223> OTHER INFORMATION: H3

<400> SEQUENCE: 27

Lys Gln Leu Ala Thr Lys Ala Ala Arg Lys Ser Ala Pro Ala Thr Gly
1               5                   10                  15

Gly Val Lys

<210> SEQ ID NO 28
<211> LENGTH: 19
<212> TYPE: PRT
<213> ORGANISM: Artificial Sequence
<220> FEATURE:
<223> OTHER INFORMATION: RORalpha

```
<400> SEQUENCE: 28

Thr Pro Leu Asn Gln Glu Ser Ala Arg Lys Ser Glu Pro Pro Ala Pro
1               5                   10                  15

Val Arg Arg
```

METHYL DEGRON PEPTIDE AND METHODS OF CONTROLLING PROTEIN LIFESPAN

CLAIM OF PRIORITY

This patent application claims priority to Korean Patent Application No. 10-2012-0112712 filed Oct. 11, 2012, the entire contents of which are incorporated herein by reference in its entirety.

BACKGROUND

1. Technical Field of the Invention

The present invention relates to an isolated methyl degron peptide and methods of controlling protein lifespan.

2. Description of the Related Art

Ubiquitination is one of the post-translational modifications which regulate not only signalling processes leading to degradation of short-lived regulatory proteins, but also acts as a recognition signal which can activate, or deactivate proteins within a signalling cascade (Pickart, 2004). The covalent attachment of ubiquitin occurs on lysine residues where E1 ubiquitin activating enzymes, E2 ubiquitin-conjugating enzymes, and E3 ubiquitin ligases work in concert (Ciechanover et al., 1982; Hershko, 1983; Hershko et al., 1983). Among the E3 ligase family members, the cullin family, found in vertebrates (e.g., CUL1, CUL2, CUL3, CUL4A, CUL4B, CUL5 and CULT) each allow interaction with specific adapters by acting as a scaffold for ubiquitin ligases (E3). CUL4 family members, including CUL4A and CUL4B, are distinct from other cullins in that they utilize more than 50 WD40-containing adapters, referred to as DCAFs (also known as VprBPs), conferring substrate specificity (Angers et al., 2006; Bennett et al., 2010; He et al., 2006; Higa et al., 2006; Jin et al., 2006).

Apart from ubiquitination, methylation is another post-translational modification that occurs on lysine residues. Among many lysine methyltransferases, Enhancer of Zeste Homolog 2 lysine methyltransferse (EZH2) is a SET domain-containing protein that exhibits histone methyltransferase activity with specificity to histone H3K27 methylation, and forms a polycomb-group repressive complex 2 (PRC2) with EED and SUZ12 (Cao et al., 2002; Caretti et al., 2004; Jones et al., 1998; Kuzmichev et al., 2004; Sewalt et al., 1999). Importantly, EZH2 has been proposed to have oncogenic activity in that it is often deregulated in a number of cancer types (Cao et al., 2011; Chang et al., 2011; Hobert et al., 1996; Kleer et al., 2003; Varambally et al., 2002), and aggressive breast and prostate cancers exhibit high levels of EZH2 which correlates with poor patient prognosis (Fukuyama et al., 2000; Jacobs and van Lohuizen, 2002).

Although nuclear receptors have a variety of different functions to regulate numerous processes by switching transcription on and off via recruiting a complex of co-regulatory proteins (Atkins et al., 1999; Glass and Rosenfeld, 2000), there is increasing evidence that some orphan nuclear receptors play a critical role in tumor suppression. Orphan nuclear receptors are ligand-activated transcription factors, for which no cognate ligands have been identified (Blumberg and Evans, 1998; Giguère, 1999), and one such orphan nuclear receptor includes retinoic acid-related orphan nuclear receptor α (RORα) which acts as an inhibitor of colon cancer growth by trans-repressing canonical Wnt/β-catenin signalling (Lee et al., 2010). DNA damage-induced RORα is involved in the positive regulation of p53 stability leading to increased apoptosis (Kim et al., 2011). RORα has been shown to reduce the migratory and invasive abilities of androgen-independent prostate cancer cells, such as DU145 cells (Moretti et al., 2002). Together, these findings suggest a tumor suppressive role of RORα.

Here, we first provide the evidence that methylation-dependent ubiquitination of RORα is carried out by DCAF1/DDB1/CUL4 E3 ubiquitin ligase complex. We identify DCAF1 as a direct adaptor linking DDB1/CUL4 to RORα by specifically recognizing mono-methylated RORα. Our studies reveal that the chromo domain in DCAF1 functions as a mono-methyl-specific reader by molecular modeling and binding affinity studies. These findings suggest a novel "methyl-degron" pathway where non-histone protein stability is dynamically regulated by methylation. Further, we present physiological data in conjunction with biochemical data strongly supporting the oncogenic role of EZH2 by facilitating RORα methylation-dependent degradation, thereby inhibiting the tumor suppressive role exerted by RORα.

BRIEF DESCRIPTION OF THE DRAWINGS

FIG. 39 shows that protein sequence alignment of the chromo domains of HP1, Pc, DCAF1, and modified DCAF1. Inserted amino acid sequences are shaded the sequence alignment.

SUMMARY

Figure 1:
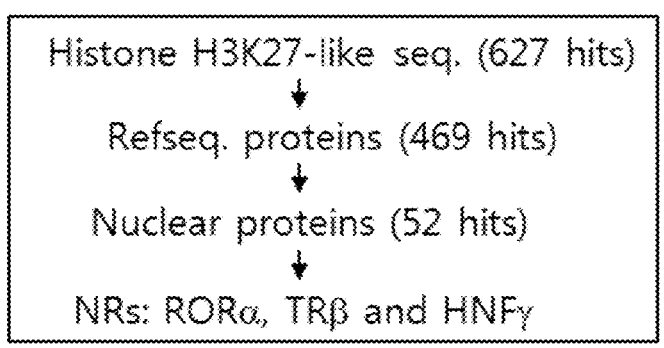
FIG. 1 shows the screening process of histone H3K27-like sequence-containing proteins used and the N-terminal domains of RORα containing histone H3K27-like sequences: *Homo sapiens* (h) and *Mus musculus* (m) forms of RORα are aligned.

It is an aspect of the present invention to provide an isolated methyl degron peptide.

Another aspect of the present invention is to provide at least one of the followings: a fusion protein comprising a methyl degron peptide of SEQ ID NO: 1; a protein obtained by mutation of the methyl degron peptide having an extended lifespan.

Still another aspect of the present invention is to provide a method for screening an agent that regulates protein lifespan.

Still yet another aspect of the present invention is to provide a method for screening an anticancer agent.

Still yet another aspect of the present invention is to provide at least one of the followings: a method of regulating protein lifespan using a methyl degron peptide of SEQ ID NO: 1; a method of regulating protein expression using a methyl degron gene sequence of SEQ ID NO: 2.

Still yet another aspect of the present invention is to provide at least one of the followings: a method of treating cancer using a methyl degron peptide of SEQ ID NO: 1; a methyl degron gene of SEQ ID NO: 2.

Yet another aspect of the present invention is to provide at least one of the followings: an isolated gene encoding the methyl degron gene; a recombinant vector comprising the methyl degron gene; a transformed host cell comprising the recombinant vector.

DETAILED DESCRIPTION

To achieve the above aspects, a first aspect of the present invention provides an isolated methyl degron peptide, an isolated methyl degron gene encoding the same, and a method of treating cancer using the methyl degron gene. More specifically, the methyl degron peptide is set forth in SEQ ID NO: 1, and the methyl degron gene is set forth in SEQ ID NO: 2.

As used herein, the term "methyl degron peptide" refers to a peptide comprising a sequence similar to that of histone present in ROR alpha (hereinafter referred to as "RORα"). Methylation of the protein is induced by Enhancer of Zeste Homolog 2 lysine methyltransferse (EZH2) in the sequence, and the methylated protein is recognized by DDB1-CUL4-associated factor 1 adaptor (DCAF1) and is involved in ubiquitin-dependent protein degradation. More specifically, the present invention provides a method for treating cancer, characterized by extending the lifespan of an anticancer-related protein by mutating the methyl degron gene, or a method for treating cancer, characterized by shortening the lifespan of a carcinogenesis-related protein using the methyl degron gene.

A second aspect of the present invention provides a fusion protein comprising the methyl degron peptide. The protein has a shortened lifespan and a carcinogenic effect.

As used herein, the term "fusion protein" refers to a protein made by combining two or more proteins encoding an isolated protein. Translation of the fusion protein results in a single polypeptide.

A third aspect of the present invention provides a protein obtained by mutation of the methyl degron peptide and having an extended lifespan. The protein provides an anticancer effect due to its extended lifespan.

When the methyl degron peptide is mutated by site-directed mutagenesis, it is not methylated by EZH2, and thus cannot be recognized by DCAF1. Thus, the lifespan of the protein is extended, because ubiquitin-dependent degradation of the protein does not occur.

A fourth aspect of the present invention provides a method for screening an agent that regulates protein lifespan, the method comprising the steps of: (a) culturing a cell; (b) treating the cell with a potential agent; (c) analyzing the degree of methylation of a methyl degron peptide in the cell; and (d) determining the potential agent to be an agent that reduces protein lifespan, when the degree of methylation is increased; and determining the potential agent to be an agent that increases protein lifespan, when the degree of methylation is decreased.

Analysis of the methylation may be performed by any one or more methods selected from the group consisting of an immunochemical method, a method using a radioisotope material, a method based on the difference in molecular weight by electrophoresis, and a method using a fluorescent dye method.

A fifth aspect of the present invention provides a method for screening an anticancer agent, the method comprising the steps of: (a) culturing a cell; (b) treating the cell with a potential agent; (c) analyzing the degree of methylation of a methyl degron peptide in the cell; (d) determining the potential agent to reduce protein lifespan, when the degree of methylation is increased, and determining the potential agent to increase protein lifespan, when the degree of methylation is decreased; and (e) determining the methylated protein to be a carcinogenesis-related protein and determining the lifespan of the carcinogenesis-related protein to be reduced.

More specifically, the cancer may be any one selected from the group consisting of breast cancer, liver cancer, bladder cancer, cervical cancer, colorectal cancer, kidney cancer, lung cancer, prostate cancer, pancreatic cancer, stomach cancer, and uterine cancer.

A sixth aspect of the present invention provides a method of regulating protein lifespan using a methyl degron peptide of SEQ ID NO: 1, and a method of regulating protein expression using a methyl degron gene sequence of SEQ ID NO: 2.

More specifically, when the methyl degron peptide is inserted, protein lifespan is shortened, and when the methyl degron peptide is mutated, protein lifespan is extended.

A seventh aspect of the present invention provides a method of treating cancers using a methyl degron peptide of SEQ ID NO: 1. More specifically, it provides a method for treating cancers, characterized in that the lifespan of an anticancer-related protein is extended by mutating the methyl degron peptide sequence, or a method for treating cancers, characterized in that the lifespan of a carcinogenesis-related protein is shortened by inserting the methyl degron peptide sequence.

An eighth aspect of the present invention provides a recombinant vector comprising the methyl degron gene.

As used herein, the term "vector" refers to a nucleic acid molecule capable of transporting another nucleic acid bound thereto. As used herein, the term "expression vector" is intended to include a plasmid, cosmid, or phage that can synthesize a protein encoded by a recombinant gene carried by the vector. A preferred vector is a vector that can self-replicate and express a nucleic acid linked thereto.

A ninth aspect of the present invention provides a host cell transformed with the recombinant vector.

As used herein, the term "transformation" means that foreign DNA or RNA is absorbed into a cell to change the genotype of the cell. Suitable examples of cells to be transformed with the recombinant vector include, but are not limited to, prokaryotic cells, fungal cells, animal cells, plant cells, and the like. Most preferably, *E. coli* cells are used.

The methyl degron sequence according to the present invention is a novel sequence that can be used to regulate protein lifespan and can be used in various fields in the regulation of protein lifespan is required. Particularly, when protein life span needs to be regulated in order to make cancer treatments effective, the protein lifespan can be regulated by inserting, deleting, or mutating the methyl degron sequence. Thus, the methyl degron sequence can be effectively used for cancer treatments. However, the use of the methyl degron sequence is not limited only to cancer treatment.

EXAMPLES

Example 1

Antibodies

The following commercially available antibodies were used: RORα (Santa Cruz Biotechnology), FLAG (Sigma), EZH2 (BD Biosciences), Xpress (Invitrogen), DDB1, CUL4B, DCAF1, H3K27me2, H3K27me3, and methyl-Lys antibodies (Abcam). RORαK38me1, RORαK38me2, and RORαK38me3 antibodies were generated by Abmart (China).

Example 2

Plasmid Construction and Site-Directed Mutagenesis

RORα K38A mutants and various GST-DCAF1 chromo domain mutants (Y563A, Y578A, P580A, and Y584A) were generated by site-directed mutagenesis using nPfu-Forte DNA polymerase (Enzynomics). 3×-Flag-CMV-RORα and GST-DCAF1 chromo domain WT were used as templates and oligonucleotides containing each mutation were used as primers.

Example 3

Liquid Chromatography-Mass Spectrometry (LC-MS)

Small quantities (100 μM) of synthetic peptides (RORα WT) were used as substrates in the HMTase assay with EZH2 enzyme; the reaction was stopped by 10% TCA precipitation for 10 min at 4° C. After removing the precipitates by centrifugation, the supernatants were retrieved and methylated peptides in the supernatants were analyzed by LC-MS. The eluted peptides were separated on a Luna column (C18 PepMap 100, 150×1 mm 5 micron) with a linear gradient (A: 100% $H_2O$, 0.1% formic acid, B: 100% ACN, 0.1% formic acid) at a flow rate of 50 mL/min. Typically, 2 μL of sample was injected. Mass spectrometry was performed on a linear ion trap mass spectrometer (LCQ DECA XP, Thermo Finnigan) coupled to a nano-LC system (NANOSPACE SI-2, Shiseido). The MS method consisted of a cycle combining one full MS scan (Mass range: 160-2000 m/z).

Example 4

Protein Stability and Image Analysis

Cells were treated with 20 μg/ml cycloheximide for various time periods, and immunoblot analyses were performed with RORα and β-actin antibodies. Images were acquired using a LSD-4000 mini chemiluminescence imager (FUJIFILM) and band intensities were quantified by densitometry with the Multi Gauge software (FUJIFILM) according to the manufacturer's instructions.

Example 5

Ubiquitination Assay

Cells were transfected with combinations of plasmids including HisMax-ubiquitin. After incubation for 48 hrs, cells were treated with MG132, lysed in buffer A (6 M guanidinium-HCl, 0.1 M $Na_2HPO_4/NaH_2PO_4$, 0.01 M Tris-Cl [pH 8.0], 5 mM imidazole, and 10 mM β-mercaptoethanol), and incubated with $Ni^{2+}$-NTA beads (Qiagen) for 4 hrs at room temperature. The beads were sequentially washed with buffer A, buffer B (8 M urea, 0.1 M $Na_2PO_4/NaH_2PO_4$, 0.01 M Tris-Cl [pH 8.0], and 10 mM β-mercaptoethanol), and buffer C (8 M urea, 0.1 M $Na_2PO_4/NaH_2PO_4$, 0.01 M Tris-Cl [pH 6.3], and 10 mM β-mercaptoethanol). Bound proteins were eluted with buffer D (200 mM imidazole, 0.15 M Tris-Cl [pH 6.7], 30% glycerol, 0.72 M β-mercaptoethanol, and 5% SDS), and subject to immunoblot analysis.

Example 6

In Vitro Peptide Binding Assay

GST-tagged DCAF1 chromo domain WT and its mutants bound to Glutathione-Sepharose beads were prepared. The beads were mixed with 100 µg of bovine serum albumin and 15 µg of RORαK38me0, RORαK38me1, H3K27me0, or H3K27me3 peptides in 1 ml of binding buffer (10 mM $Na_2HPO_4$, 2.7 mM KCl, 1.8 mM $KH_2PO_4$, and 140 mM NaCl, pH 7.4) supplemented with 1 mM phenylmethylsulfonyl fluoride and 2 mM dithiothreitol followed by incubation at room temperature for 2 h. After washing with the binding buffer, the protein with bound peptide was eluted with 6.8 mg/ml of Glutathione in Tris-HCl (pH 8.0) buffer and visualized by dot blot analysis.

Example 7

Homology Modelling

The homology modelling of the cDCAF1 in complex with RORα peptide (L31-S39) was performed using DS MODELER (Sali and Blundell, 1993). Chromo domains of HP (PDB id: 1KNA) and Pc (PDB id: 1PDQ) served as templates, and the H3 tail peptide in the template was substituted by the RORα peptide for modelling the cDCAF1-RORα structure. The generated model was simulated by the standard dynamics cascade protocol of DS CHARMm with the CHARMm forcefield (Brooks et al., 1983). Constraints were applied to all backbone atoms of cDCAF1 during simulations. An explicit periodic boundary model was applied to solvate the molecule in water. The 3000-step minimization was performed using the steepest descent method, and followed by a 3000-step minimization via the conjugate gradient method. After minimization, the complex structure was heated to 300 K and equilibrated for 700 ps. Finally, a molecular dynamics simulation at 300 K for 1 ns was performed. In all dynamics simulations, the time step was 1 fs and the cut-off distance related to the intermolecular interactions was 14 Å. The lowest energy structure of the final simulation was selected for structural analysis. The modified cDCAF1 containing the extra three insertions (Y578^G579insK, Y584^W585insNT) was modelled in DS MODELER, and overlapped onto the chromo domain of Pc. The method for molecular dynamics simulation of the modified cDCAF1 in complex with histone peptide containing the trimethylated Lys was virtually the same as described for cDCAF1-RORα. The overall stereochemical quality of the refined models was evaluated by the PROCHECK program (Laskowski et al., 1993).

Example 8

Cell Transformation Assay

Anchorage-independent growth of MCF7 breast cancer cells stably expressing empty vector or RORα or cells transfected with control siRNA or DCAF1 siRNAs or treated in the presence and absence of DANep (2 µM) were determined by analysing colony formation in soft agar. Cells ($10^5$) were placed in DMEM media containing 0.4% noble agar containing 10% FBS for 3 weeks in 5% $CO_2$, and colonies exhibiting greater than 100 µM were counted and analysed.

Example 9

Human Breast Cancer Tissue Specimens

For the analysis of RORα and EZH2 protein expression in human tissue samples, 43 paired fresh frozen breast cancer tissues and matched normal tissues were selected. The frozen fresh human tissue specimens were supplied from Seoul National University Hospital. Immunoblot images were acquired using a LSD-4000 mini chemiluminescence imager (FUJIFILM), and band intensities were quantified by densitometry with the Multi Gauge software (FUJIFILM) according to the manufacturer's instructions.

Example 10

EZH2 Methyltransferase-Mediated Mono-Methylation of RORα at K38

Figure 2:
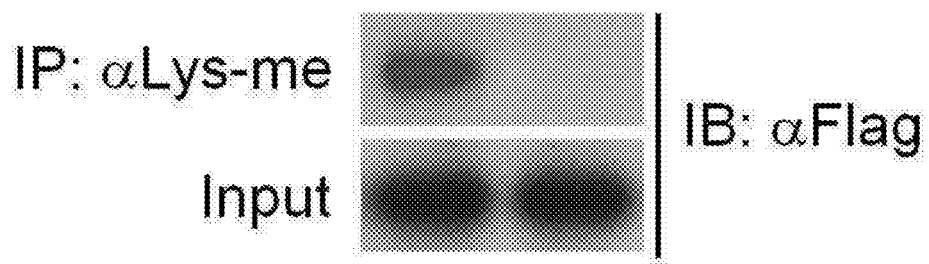
FIG. 2 shows HEK-293 cells transfected with expression constructs for Flag-RORα, WT, or K38A mutants. A co-immunoprecipitation assay was conducted with an anti-lysine methyl antibody and the precipitates were analyzed by immunoblot with anti-Flag antibody to detect RORα.

Although some methyltransferases have been shown to act on transcription factors and histone modifiers as well as histones in the nucleus, the possibility of there being distinct substrate specificity for histones and non-histone proteins for the same methyltransferase has not been extensively studied. Given that not much is known about the non-histone substrates of EZH2 thus far, we intended to identify and compare their substrate specificity with histone substrates, and explore their underlying mechanisms. We computationally screened for proteins having similar amino acid sequences to the region in histone H3K27 methylated by EZH2, namely the amino acid sequence "R-K-S" (FIG. 1). From this screening, 627 proteins came out as 'hits' and we considered 469 proteins that were annotated and curated from The Reference Sequence (RefSeq) database. The Database for Annotation, Visualization and Integrated Discovery (DAVID) Bioinformatics Resource (David Bioinformatics Resources) provides a rapid means to reduce large lists of genes into functionally related groups of genes to help unravel the biological content captured by high throughput technologies. Therefore, we utilized DAVID to perform functional annotation and clustering of these proteins. There were several categories of protein function, and we looked closely into 52 proteins that were involved in transcriptional regulation. We selected one orphan nuclear receptor RORα (Giguère et al., 1994; Hamilton et al., 1996; Kim et al., 2011; Lee et al., 2010) out of three nuclear receptors that were present in this group. The "R-K-S" sequence was located within the N-terminal domain of RORα and was thus speculated to serve as an acceptor site for methylation (FIG. 1). Therefore, we hypothesized that the histone-like sequence in RORα might allow for RORα K38 methylation by a H3K27 histone methyltransferase, exemplified by EZH2, and we generated a K38A mutant in which a lysine residue was replaced by an alanine to abrogate lysine methylation. Co-immunoprecipitation assay revealed that K38A mutation abrogated RORα methylation, suggesting that K38 is the methyl-acceptor site of RORα (FIG. 2).

Figure 3:
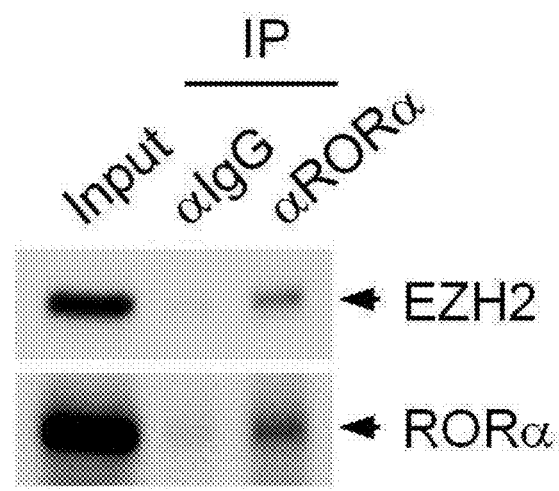
FIG. 3 shows that a co-immunoprecipitation assay was performed to detect the interaction between the endogenous RORα and EZH2 in HEK-293 cells treated with MG132.
Figure 4:
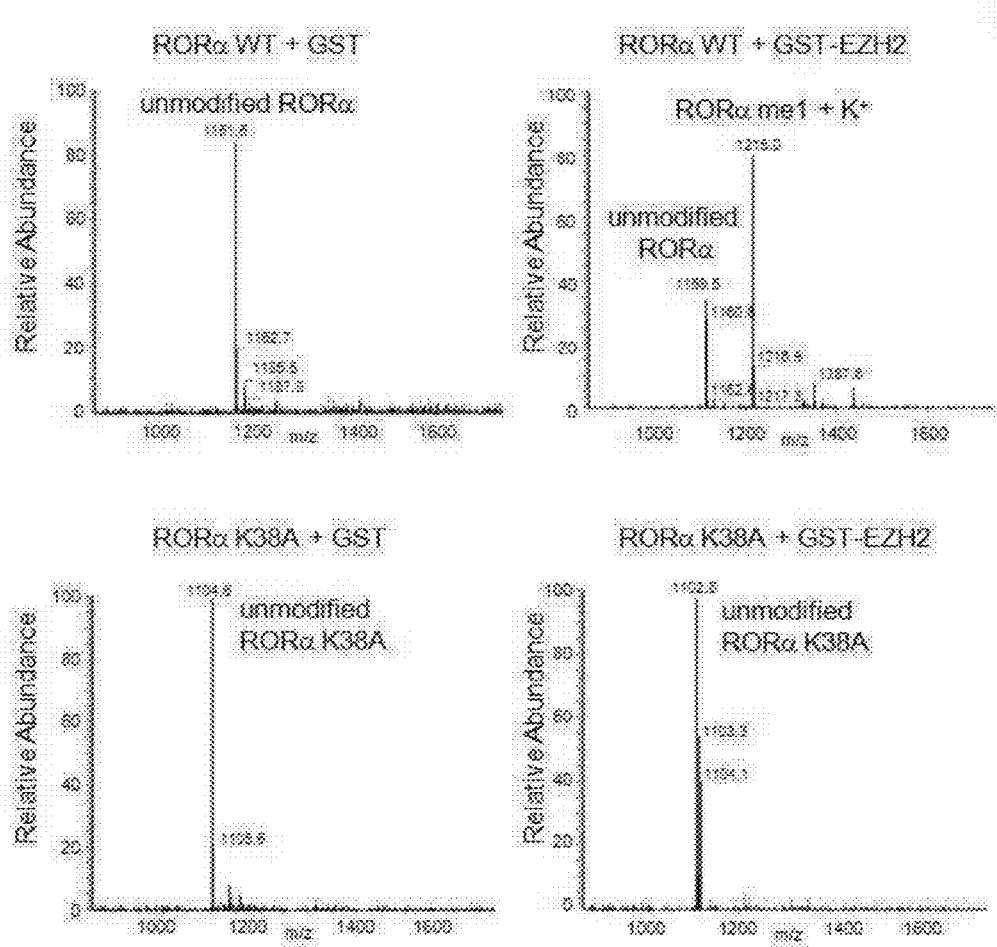
FIG. 4 shows the mass spectrometric analysis of RORα WT and K38A used following a methyltransferase assay using either GST or GST-EZH2.

The association of EZH2 with RORα at endogenous levels was confirmed by co-immunoprecipitation analysis (FIG. 3). To assess whether RORα is methylated by EZH2 and to determine the methylation status of RORα, peptides bearing amino acids 31-40 of RORα (LNQESARKSE) were in vitro methylated by EZH2 and analyzed by mass spectrometry. The non-methylated RORα wild-type (WT) peptide had its main peak at 1161.6 Da, while the mono-methylated peptides appeared at 1215 Da, with the 38-Da mass of potassium (K$^+$) incorporated during the peptide sample preparation after the histone methyltransferase assay with EZH2 (FIG. 4). On the other hand, there was no detectable alteration in the methylation state of RORα K38A by EZH2 (FIG. 4). Together, these data indicate that EZH2 induced the addition of one methyl group to the K38 site.

Figure 5:
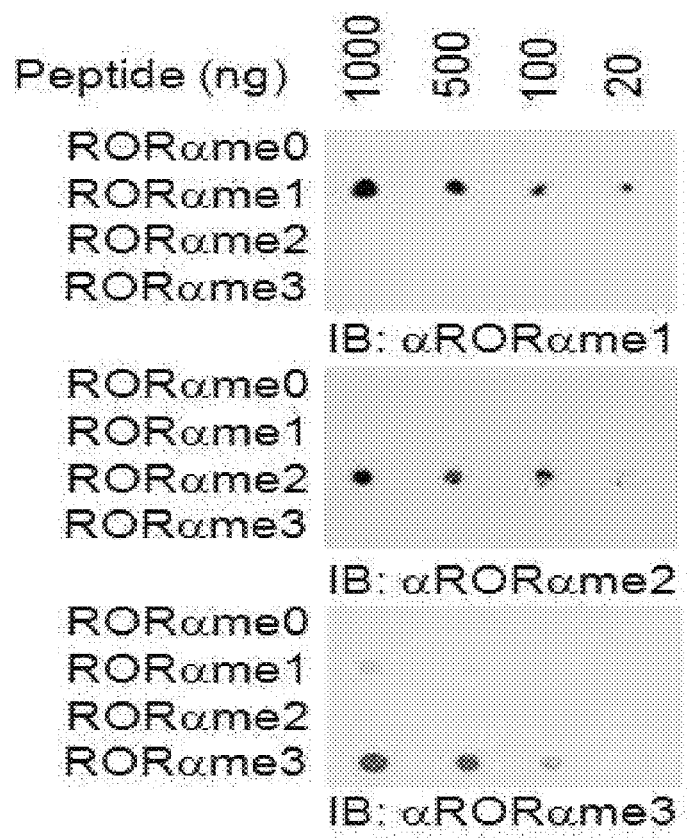
FIG. 5 shows that the specificity of antibodies against mono-, di-, or tri-methyl RORα K38 was assessed by dot blot analysis.
Figure 6:
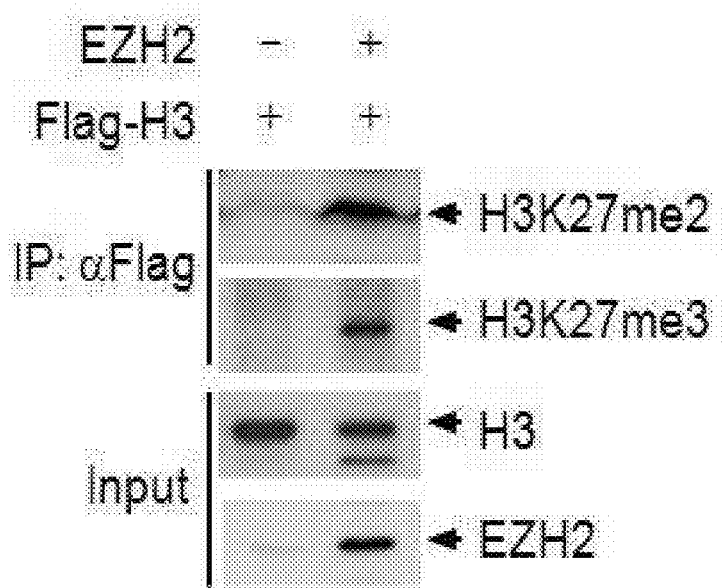
FIG. 6 shows that Flag-histone H3 was expressed in HEK-293 cells and immunoprecipitated with anti-Flag antibody in the presence or absence of EZH2. H3K27 methylation was examined by immunoblot using anti-H3K27me2 and H3K27me3 antibodies.
Figure 7:
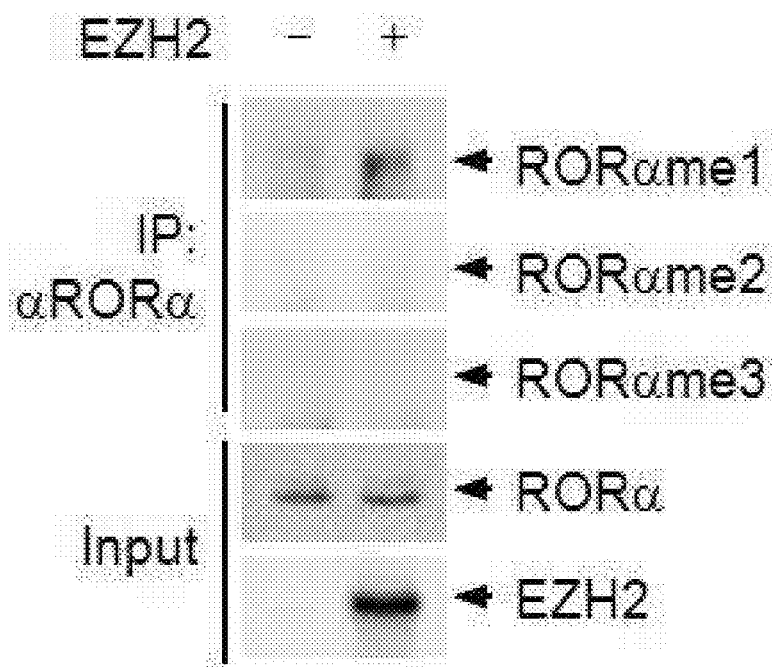
FIG. 7 shows that an immunoprecipitation assay was performed with anti-RORα antibody in the absence or presence of EZH2 with MG132 treatment. RORα methylation was examined by immunoblot using anti-mono-, di-, or tri-methyl RORα antibodies.
Figure 8:
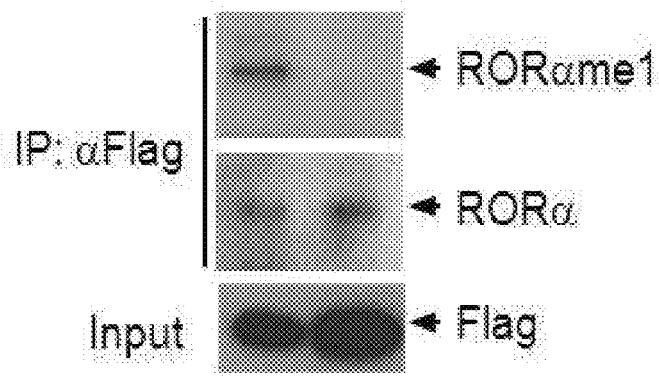
FIG. 8 shows that Flag-RORα WT or K38A mutant was expressed in HEK-293 cells and immunoprecipitated with anti-Flag antibody, followed by immunoblot with anti-RORαme1 antibody.
Figure 9:
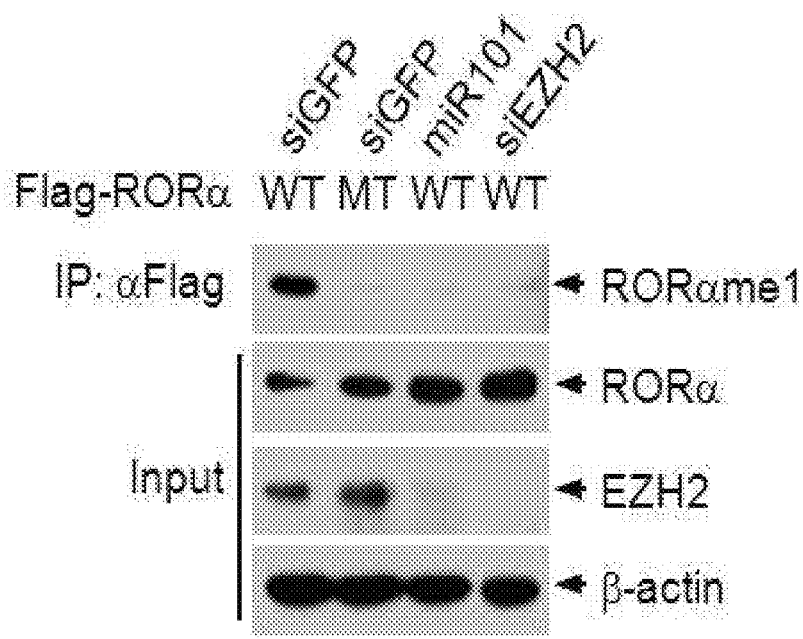
FIG. 9 shows that control siRNA against GFP, miR101, and siRNA against EZH2 were transfected along with Flag-RORα WT and K38A mutants. After immunoprecipitation with anti-Flag antibody, mono-methylation levels of RORα were detected by anti-RORαme1 antibody.

Since EZH2 has histone substrate specificity of di- and trimethylation of H3K27, the unexpected finding of monomethylation of RORα, a non-histone substrate, allowed us to explore whether EZH2 has distinct substrate specificity for histones and non-histone proteins. Therefore, we generated RORα K38 mono-, di-, or trimethyl-specific antibodies, while ensuring that they had no cross-reactivity with the non-methylated RORα peptide (FIG. 5). Although EZH2 is capable of generating mainly di- and trimethylated histone H3K27 (FIG. 6), only mono-methylation of RORα was detected at the K38 site by the ectopic expression of EZH2 ((FIG. 7). Immunoprecipitation assay confirmed that the RORα K38A mutant failed to be recognized by an anti-RORα mono-methyl-specific antibody (FIG. 8). Further, knockdown of EZH2 by specific siRNA or miR101 caused a marked decrease in the mono-methylation of RORα (FIG. 9). Based on these results, we concluded that EZH2-mediated mono-methylation occurs on RORα K38.

Example 11

EZH2-Mediated RORα Methylation Destabilizes RORα

Figure 10:
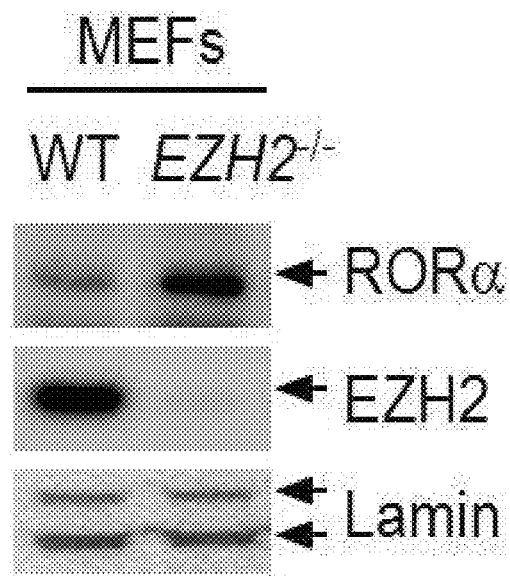
FIG. 10 shows that EZH2 and RORα protein levels in WT and EZH2-deficient (KO) MEFs were compared.
Figure 11:
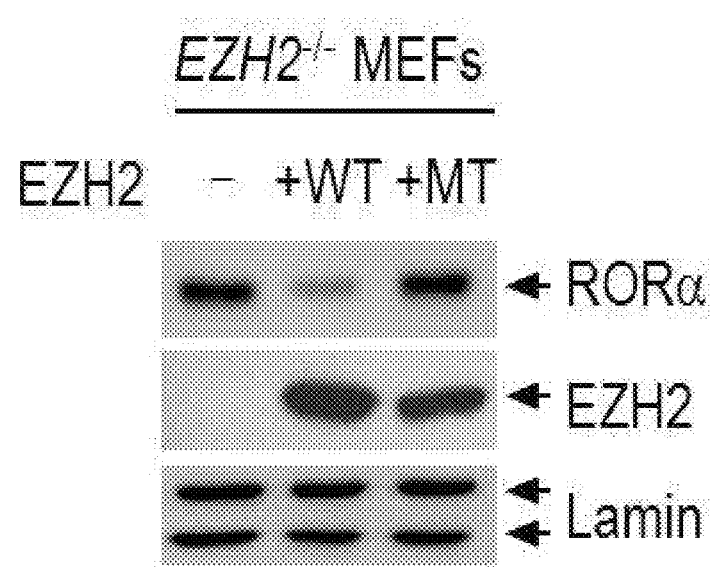
FIG. 11 shows that Ezh2-KO MEFs were reconstituted with either WT or a catalytically inactive mutant (MT) of EZH2, and changes in RORα protein levels were detected.
Figure 12:
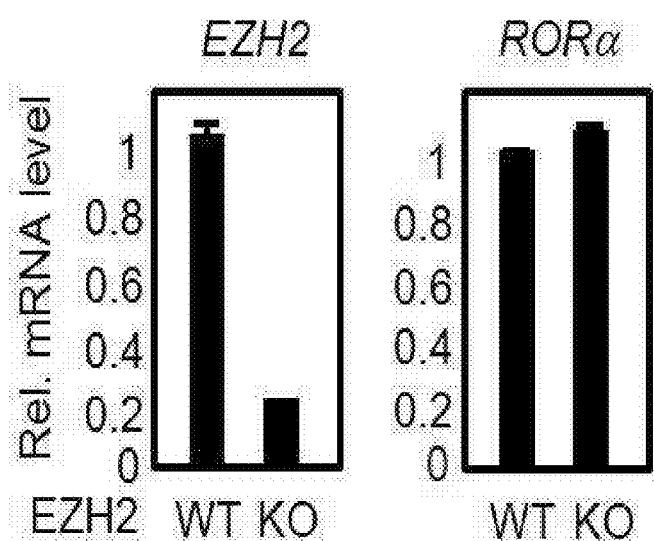
FIG. 12 shows that mRNA levels of EZH2 and RORα were measured in WT and Ezh2-KO MEFs.
Figure 13:
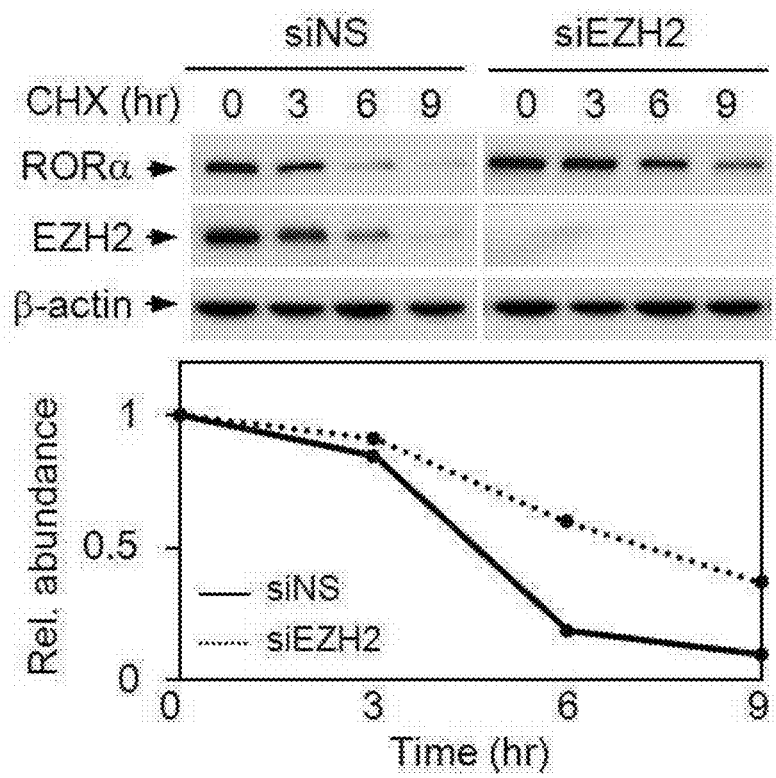
FIG. 13 and FIG. 14 show that HEK-293 cells were transfected with the indicated siRNAs (FIG. 13) and EZH2 WT/MT expression constructs (FIG. 14), and samples were collected after cycloheximide (20 µg/ml) treatment at the indicated time to determine the protein levels of RORα.
Figure 14:
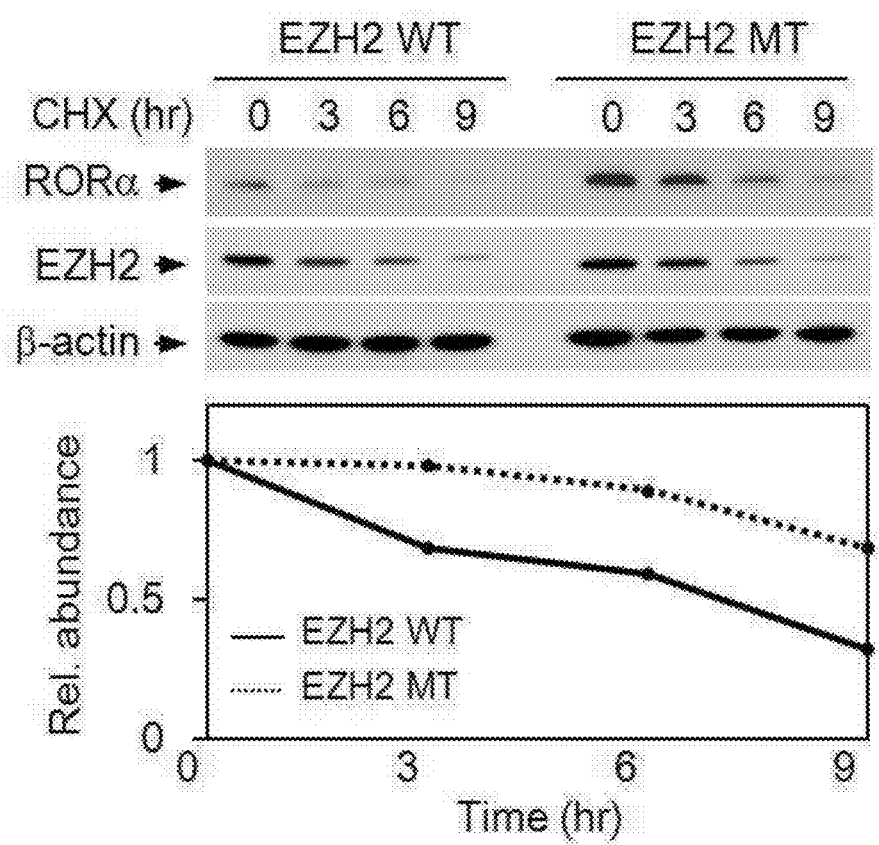

We then attempted to address the functional consequences of the EZH2-mediated RORα lysine methylation. We compared the protein expression levels of RORα in WT and EZH2-knockout (Ezh2$^{-/-}$) mouse embryonic fibroblasts (MEFs). Interestingly, the RORα protein levels were significantly increased in Ezh2$^{-/-}$ MEFs as compared to WT MEFs (FIG. 10). Reconstitution of EZH2 WT or H689A mutant (MT) of EZH2, which is the catalytically inactive mutant of EZH2, revealed that RORα protein levels were reduced only in EZH2 WT-reconstituted Ezh2$^{-/-}$ MEFs (FIG. 11). Under these conditions, however, the mRNA levels of RORα were not affected (FIG. 12), suggesting that EZH2 influences RORα protein stability. Therefore, we further examined an inverse correlation between the EZH2 and RORα protein expression. The lifespan of endogenous RORα was significantly increased by EZH2 knockdown with the treatment with the protein synthesis inhibitor, cycloheximide (CHX)(FIG. 13). To examine whether the enzymatic activity of EZH2 is directly required for the regulation of RORα protein stability, we monitored the lifespan of RORα by overexpressing EZH2 WT or EZH2 MT. The overexpression of EZH2 MT increased the lifespan of RORα in cells treated with CHX (FIG. 14), suggesting that the histone methyltransferase activity of EZH2 is required for the regulation of RORα protein stability.

Figure 15:
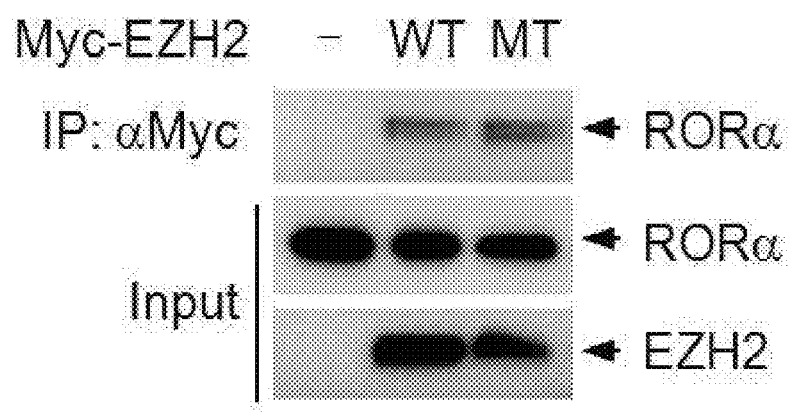
FIG. 15 shows that the binding affinity of EZH2 WT or MT with RORα was assessed.
Figure 16:
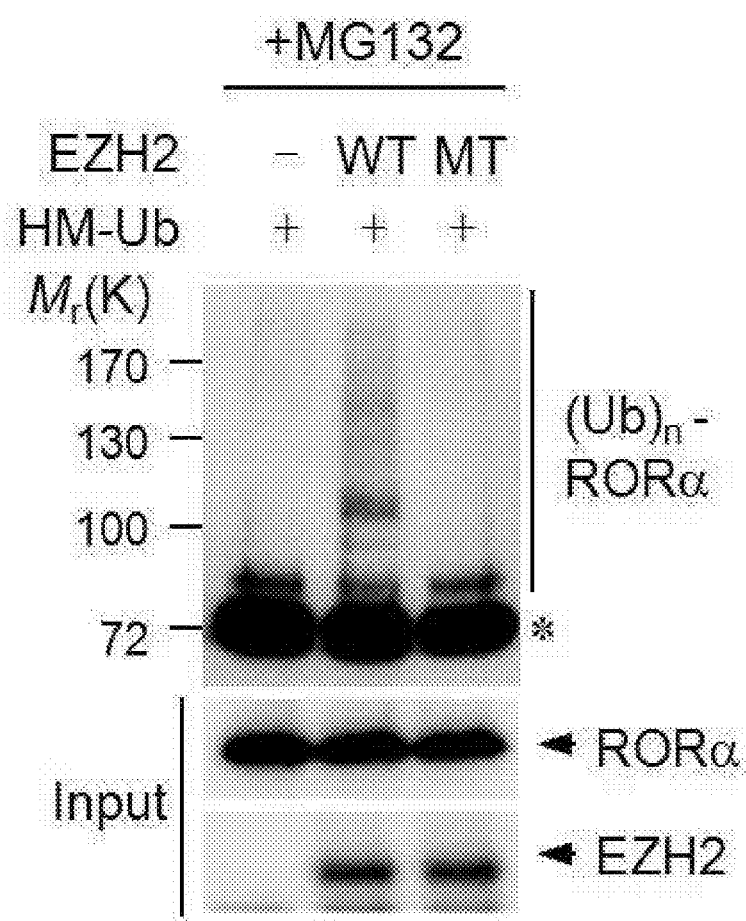
FIG. 16 shows that protein extracts from HEK-293 cells co-transfected with Flag-RORα, HisMax-ubiquitin, and EZH2 WT or MT were subjected to pull-down with $Ni^{2+}$-NTA beads.
Figure 17:
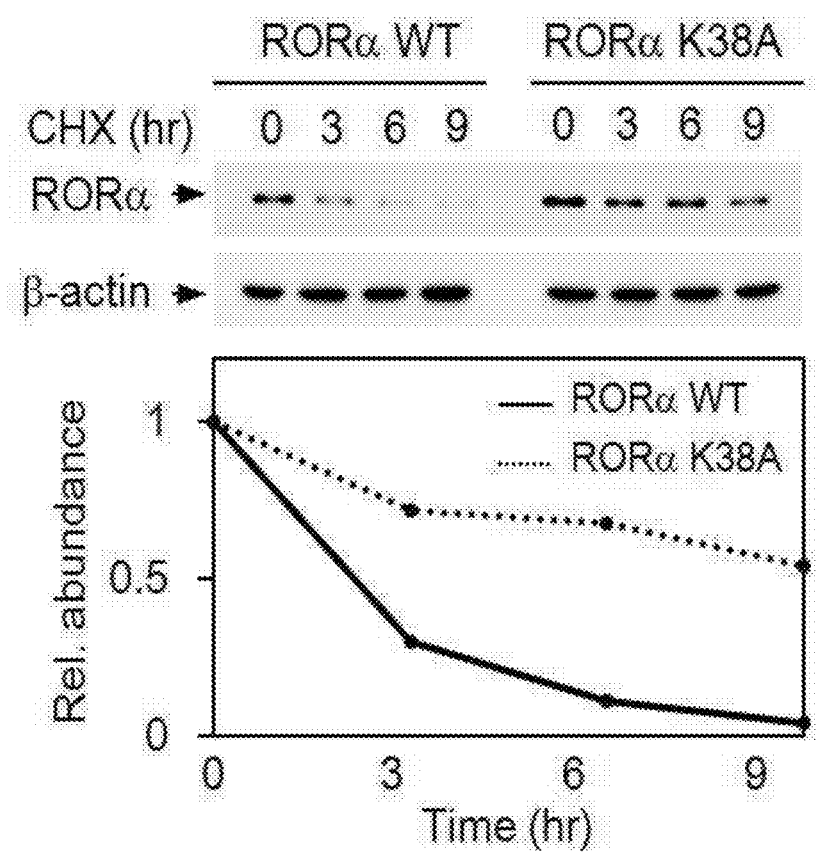
FIG. 17 shows that the lifespan of RORα WT and K38A mutant was compared in HEK-293 cells. The transfected cells were treated with cycloheximide (20 µg/ml), collected at the indicated times, and analyzed by immunoblot to determine RORα protein levels.
Figure 18:
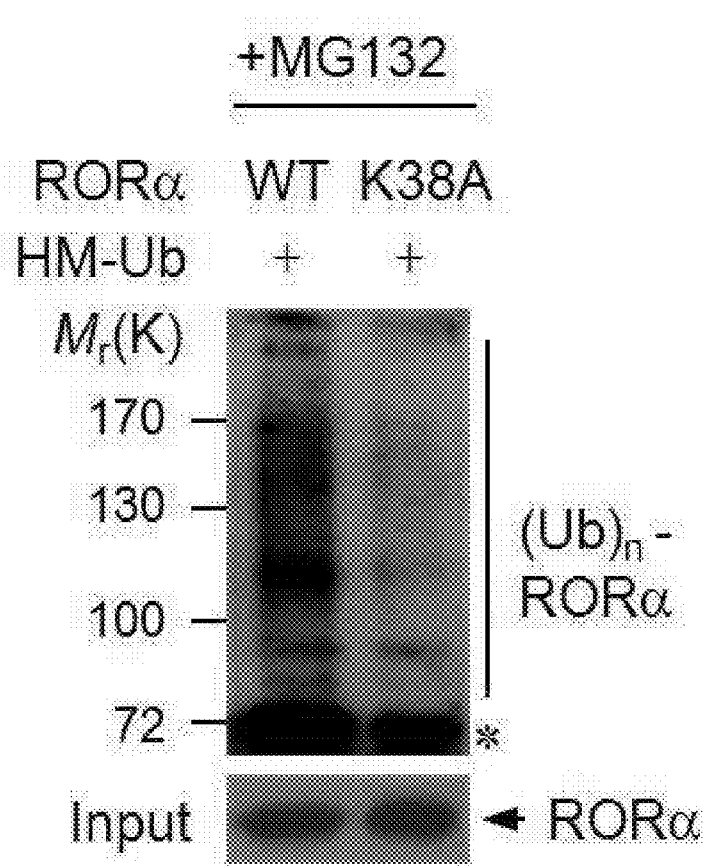
FIG. 18 shows that protein extracts from HEK-293 cells co-transfected with Flag-RORα WT or K38A mutant along with HisMax-ubiquitin were subjected to pull-down with $Ni^{2+}$-NTA beads. Ubiquitination of RORα was determined using anti-Flag antibody.
Figure 19:
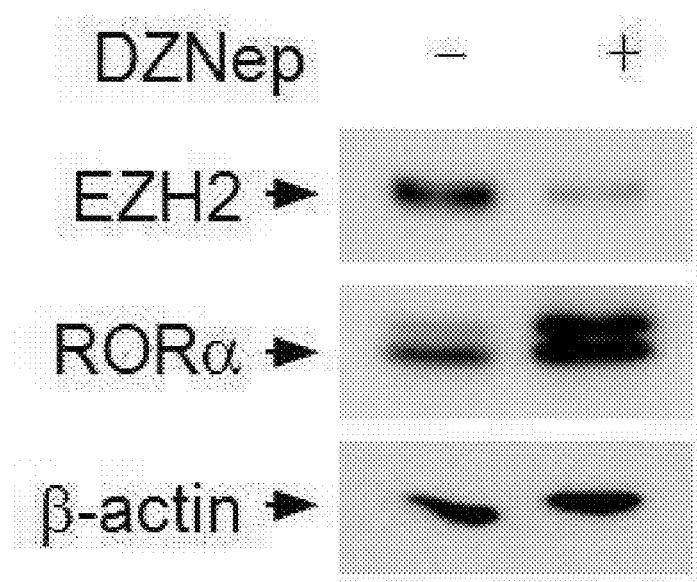
FIG. 19 shows that immunoblot analysis was performed to detect EZH2 and RORα protein levels in the absence or presence of DZNep (1 µM, 24 hr) in MCF7 cells.
Figure 20:
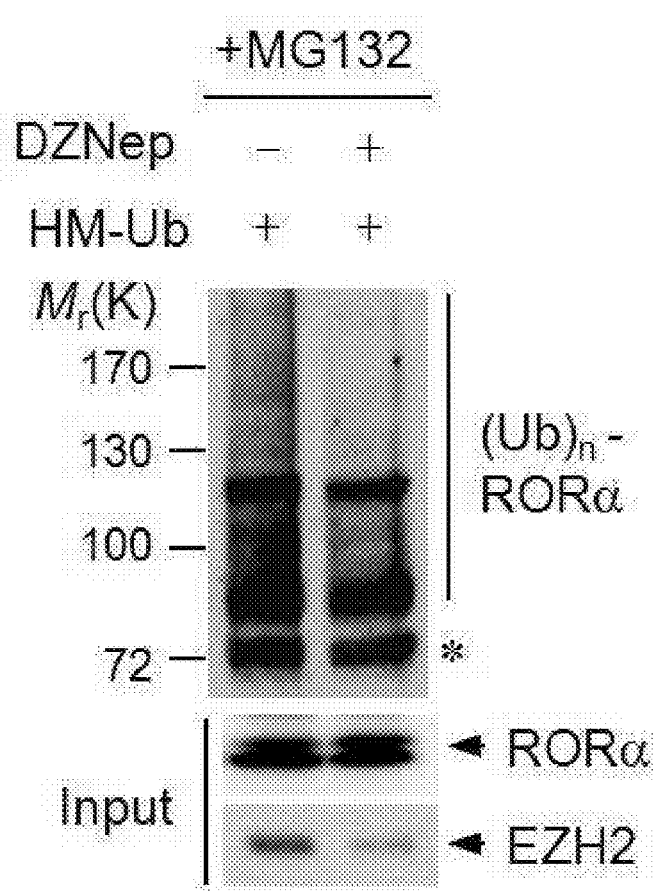
FIG. 20 shows that a RORα ubiquitination assay was conducted in the absence or presence of DZNep (1 µM, 24 hr) in HEK-293T cells.

In order to determine whether the ubiquitin-proteasome pathway is responsible for RORα degradation and to further examine whether the introduction of EZH2 augments RORα ubiquitination by allowing increased RORα methylation, we performed an RORα ubiquitination assay with EZH2 in the presence of a 26S proteasome inhibitor, MG132. Although both EZH2 WT and EZH2 MT bound to RORα readily (FIG. 15), only EZH2 WT was able to increase RORα ubiquitination (FIG. 16), indicating that the ability of EZH2 to enhance RORα ubiquitination requires the histone methyltransferase activity of EZH2. Moreover, RORα K38A mutation also markedly stabilized its protein levels (FIG. 17), suggesting that RORα degradation relies on K38 methylation. To further examine whether K38 methylation directly affects RORα ubiquitination, we performed a ubiquitination assay for RORα WT and RORα K38A in the presence of MG132. Indeed, RORα K38A mutation led to a marked reduction in RORα ubiquitination compared to RORα WT (FIG. 18). Next, we examined whether an EZH2 small molecule inhibitor, exemplified by DZNep, rescues the EZH2-mediated degradation of RORα. Treatment with DZNep led to the reduction of EZH2 protein levels and increases in RORα protein levels (FIG. 19). We compared RORα ubiquitination levels in the presence and absence of DZNep, and found that RORα ubiquitination levels were decreased with the treatment of DZNep (FIG. 20). Together, these results indicate that K38 mono-methylation by EZH2 is a prerequisite for RORα degradation through the ubiquitin-proteasome pathway.

Example 12

Identification of DCAF1 Selectively Recognizing Mono-Methylated Substrates

Figure 21:
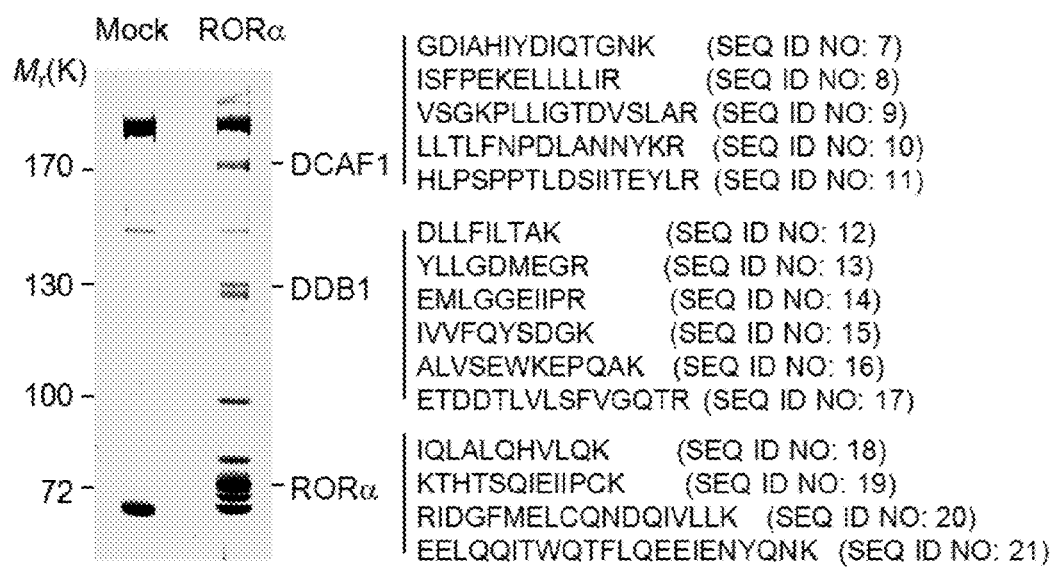
FIG. 21 shows that RORα-interacting proteins were purified from HEK-293 cells stably expressing Flag-RORα in the presence of MG132 by co-immunoprecipitation with anti-Flag antibody. As a negative control, cells expressing a Flag empty vector were used. Bound proteins were resolved via SDS-PAGE and prepared for LC-MS/MS analysis. DCAF1 and DDB1 were detected as RORα-interacting proteins.
Figure 22:
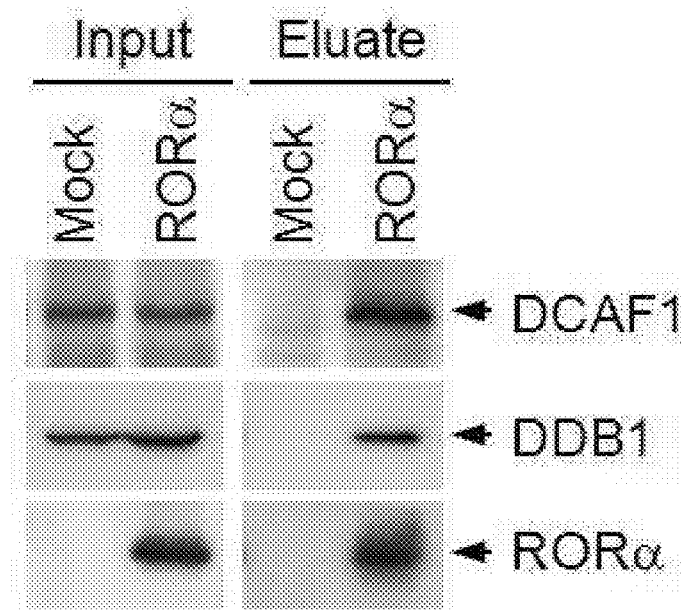
FIG. 22 shows that the binding of DCAF1 or DDB1 with RORα was detected from the eluate by immunoblot analysis.

We hypothesized that certain substrate receptor proteins, possessing a methyl-recognition domain such as a chromo domain (Cavalli and Paro, 1998; Fischle et al., 2003; Flanagan et al., 2005; Kim et al., 2006; Maurer-Stroh et al., 2003; Min et al., 2003; Sun et al., 2008), might be required for linking mono-methylated substrates to ubiquitin-dependent degradation machinery. Therefore, we looked for RORα-interacting proteins by affinity chromatography in the presence of MG132 to block the ubiquitin-dependent degradation pathway, followed by liquid chromatography mass spectrometry/mass spectrometry (LC-MS/MS) analysis (FIG. 21). Intriguingly, DDB1 and DCAF1 were identified as RORα-binding proteins which were previously reported to be components of a CUL4-containing complex (Angers et al., 2006; Higa et al., 2006; Nishitani et al., 2006). (He et al., 2006; Jin et al., 2006) In mammals, two closely related types of CUL4, CUL4A and CUL4B have been identified, and the CUL4 E3 ligase differs from other cullin family members in that it employs the WD40-like repeat-containing protein DDB1 as an adaptor (Hu et al., 2004; Hu et al., 2008; Wang et al., 2006). The association of DCAF1 and DDB1 with RORα was further confirmed by immunoblot analysis from eluates using specific antibodies (FIG. 22).

Figure 23:
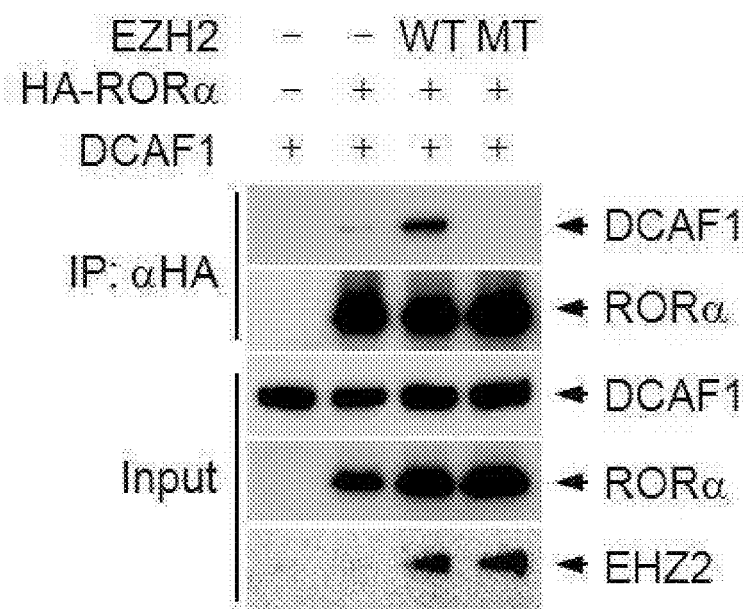
FIG. 23 shows co-immunoprecipitation of DCAF1 and RORα in HEK-293 cells treated with 20 µM of MG132 for 4 hrs. Overexpression of EZH2 WT, but not EZH2 MT, increased the binding between DCAF1 and RORα.
Figure 24:
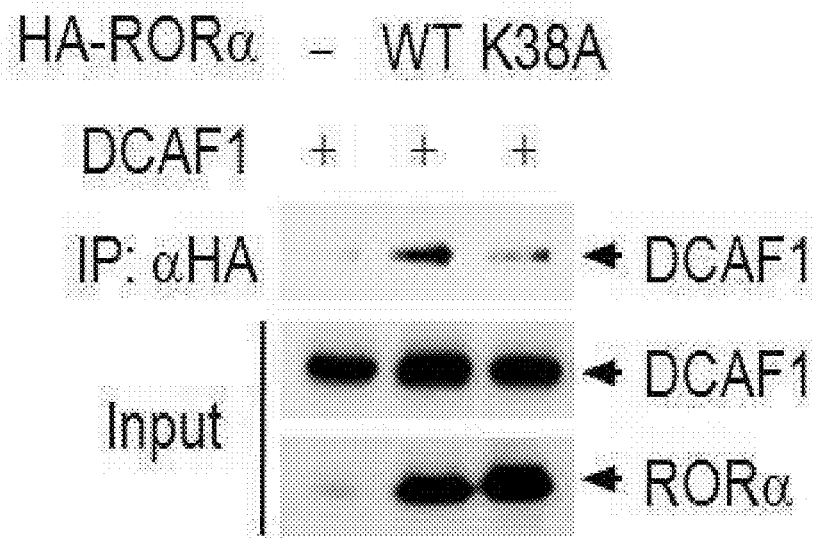
FIG. 24 shows that the binding affinity of RORα WT or K38A mutant with DCAF1 was assessed in HEK-293 cells expressing the indicated constructs treated with MG132.
Figure 25:
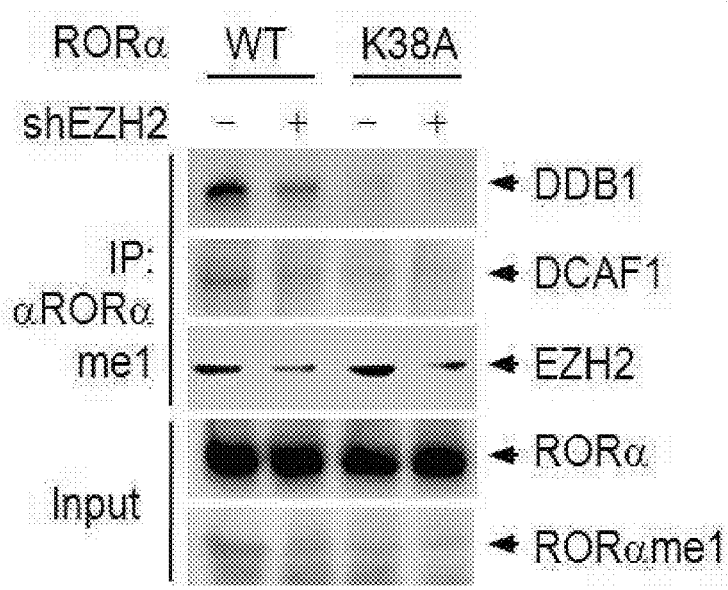
FIG. 25 shows that HEK-293 cells were transfected with EZH2 shRNA and the indicated expression constructs in the presence of MG132. A co-immunoprecipitation assay was performed to detect EZH2-dependent interaction of endogenous DCAF1 or DDB1 with RORα using anti-RORαme1 antibody.

Although post-translational modifications such as phosphorylation, glycosylation, and proline hydroxylation are required to generate specific 'degron' for the recognition of cullin-based E3 ligases (Bruick and McKnight, 2001; Ivan et al., 2001; Westbrook et al., 2008; Wu et al., 2007; Yim et al., 2009), the molecular basis of recognition of methylated substrates has not been reported. To examine the possibility that DCAF1 serves as a substrate receptor possessing a methyl-binding domain for the recognition of methylated RORα, and thereby subsequent ubiquitination and degradation, we performed a co-immunoprecipitation assay of DCAF1 with RORα in the presence of EZH2 WT or MT. Indeed, the introduction of EZH2 WT, but not EZH2 MT, significantly enhanced the binding of RORα to DCAF1 (FIG. 23). In order to further determine whether this interaction between RORα and DCAF1 is methylation-dependent, we performed co-immunoprecipitation assays comparing RORα WT and K38A mutant. The association between RORα and DCAF1 appeared to be methylation-dependent, as only RORα WT was able to interact with DCAF1, whereas RORα K38A exhibited significantly reduced interactions (FIG. 24). In accordance with the methylation-dependent binding of RORα to DCAF1, immunoprecipitation assays were performed with an anti-RORα K38 monomethyl-specific antibody with or without EZH2 knockdown. EZH2 knockdown significantly reduced RORα WT binding to DCAF1 and DDB1 while RORα K38A mutant failed to show significant interactions with DCAF1 and DDB1 (FIG. 25). Together, these data suggest that EZH2-dependent RORα methylation is crucial for binding to DCAF1.

Figure 26:
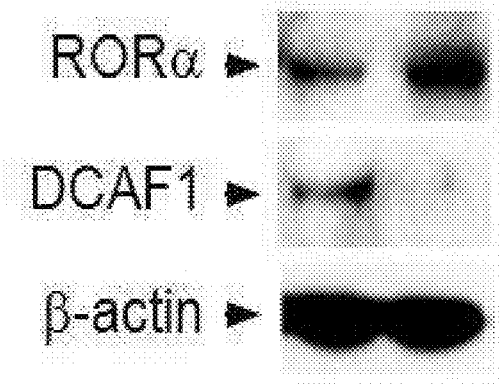
FIG. 26 shows that DCAF1 and RORα protein levels were compared between WT and Dcaf1-knockout MEFs.
Figure 27:
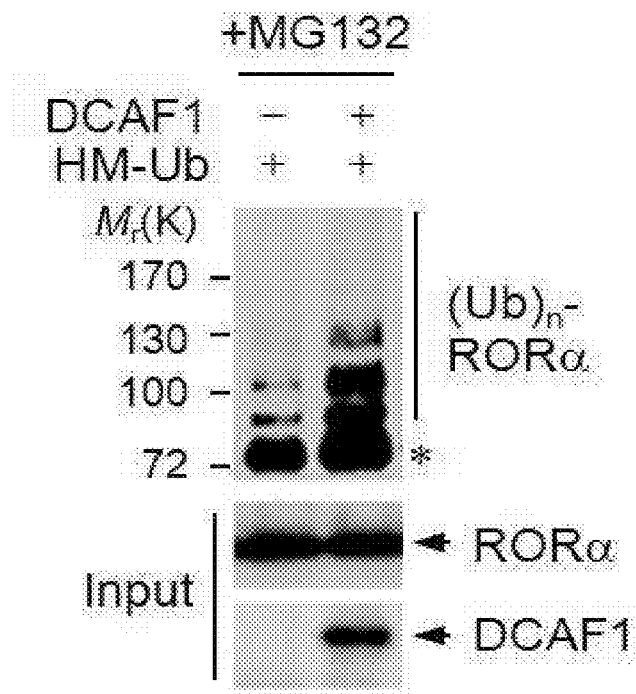
FIG. 27 shows that protein extracts from HEK-293 cells co-transfected with RORα, HisMax-ubiquitin, and DCAF1 were subjected to pull-down with $Ni^{2+}$-NTA beads.
Figure 28:
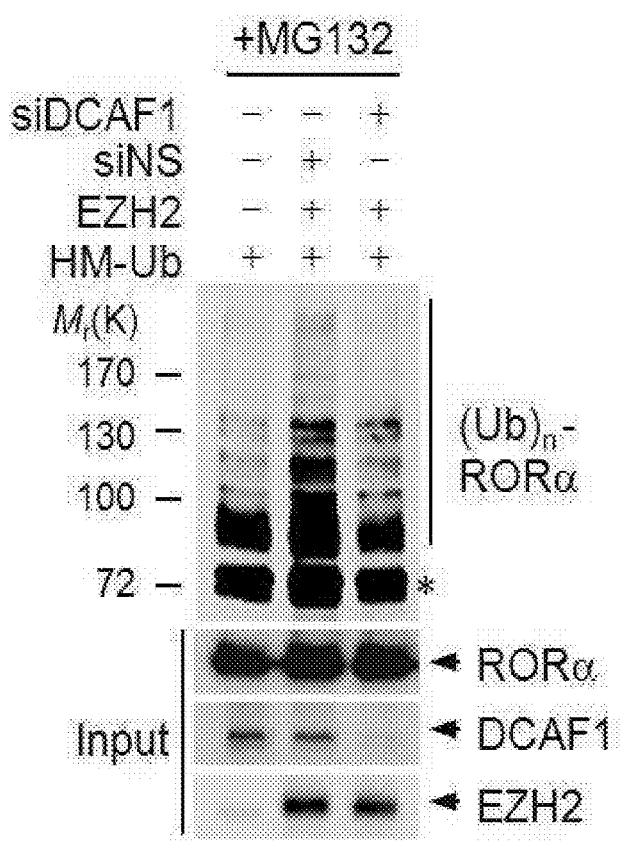
FIG. 28 shows that the enhanced RORα ubiquitination by EZH2 was decreased by DCAF1 knockdown.
Figure 29:
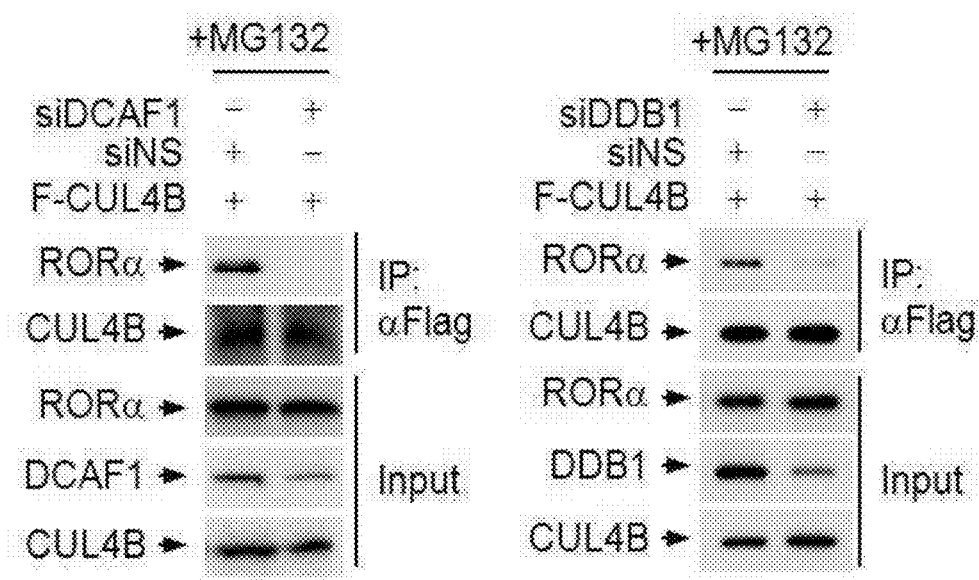
FIG. 29 shows that knockdown of DCAF1 or DDB1 decreased the binding of CUL4B to RORα.
Figure 30:
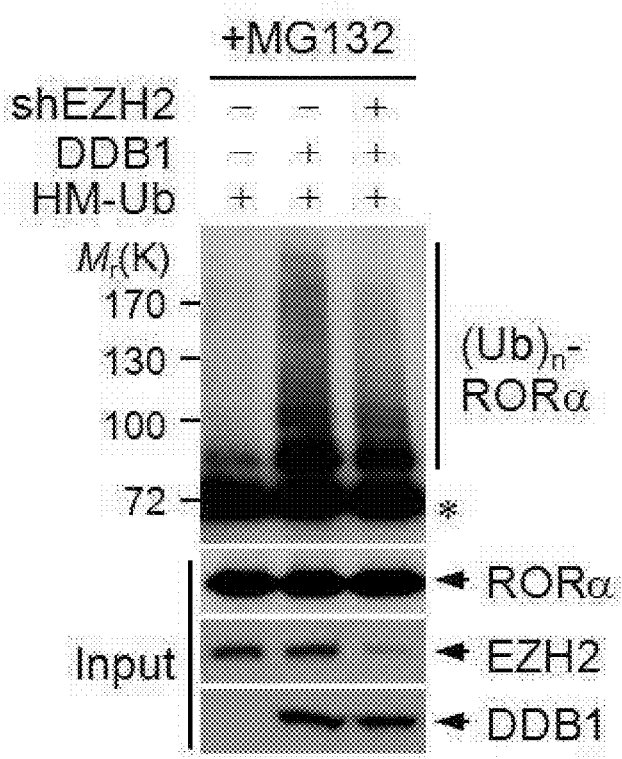
FIG. 30 shows that ubiquitination of RORα mediated by DDB1 was decreased by knockdown of EZH2.

Next, we examined whether DCAF1 directly affects RORα protein stability. Indeed, the protein levels of RORα in DCAF1-knockout MEFs (Dcaf1$^{-/-}$) were much higher than that in WT MEFs (FIG. 26). In order to further examine whether DCAF1 serves as a functional substrate receptor linking methylated substrates to subsequent ubiquitination-dependent degradation pathways, we performed an RORα ubiquitination assay. The increased DCAF1 expression enhanced RORα ubiquitination (FIG. 27). We next examined whether DCAF1 and EZH2 combine to control RORα stability via the ubiquitin-proteasome pathway. Indeed, introduction of EZH2 drastically increased the ubiquitination of RORα, whereas knockdown of DCAF1 led to a significant decrease in the ubiquitination of RORα (FIG. 28). Knockdown of DCAF1 significantly decreased the binding of RORα to CUL4B (FIG. 28). Based on the finding of DDB1 as a RORα-binding protein by affinity chromatography (FIG. 21), we examined whether knockdown of DDB1 also affects the binding of RORα to CUL4B as DCAF1 does. Knockdown of DDB1 significantly decreased the binding of RORα to CUL4B (FIG. 29). We then performed an in vivo ubiquitination assay to examine whether DDB1 and EZH2 combine to control RORα ubiquitination in the absence or presence of DDB1. Consistently, introduction of DDB1 increased the ubiquitination of RORα, and knockdown of EZH2 led to a significant decrease in the ubiquitination of RORα (FIG. 30). Together, these data indicate that DCAF1 and DDB1 are required for EZH2-dependent RORα ubiquitination.

Figure 31:
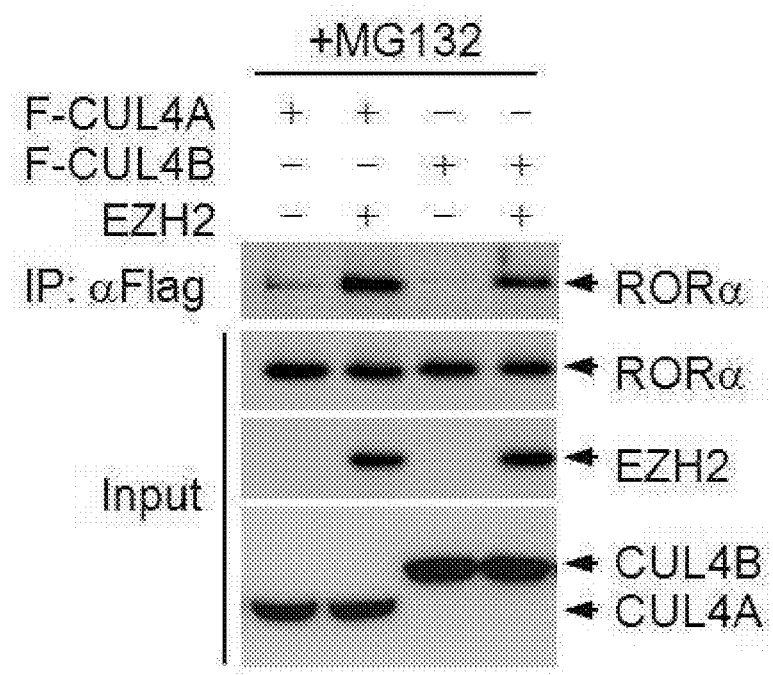
FIG. 31 shows that HEK-293 cells were transfected with Flag-CUL4A or CUL4B, and a co-immunoprecipitation assay was performed using anti-Flag antibody in the absence or presence of EZH2, followed by immunoblot analysis using anti-RORα antibody.
Figure 32:
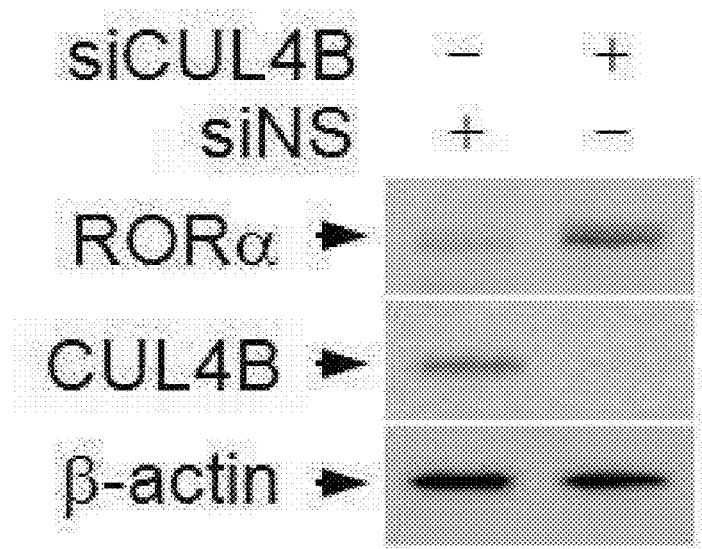
FIG. 32 shows that knockdown of CUL4B increased RORα protein levels.
Figure 33:
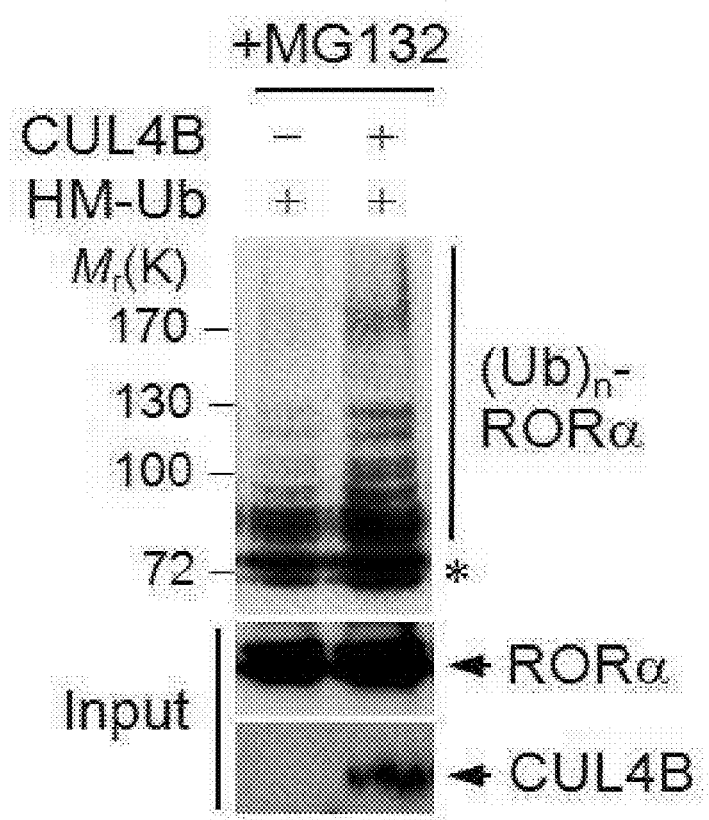
FIG. 33 shows that ubiquitination of RORα was increased by CUL4B.
Figure 34:
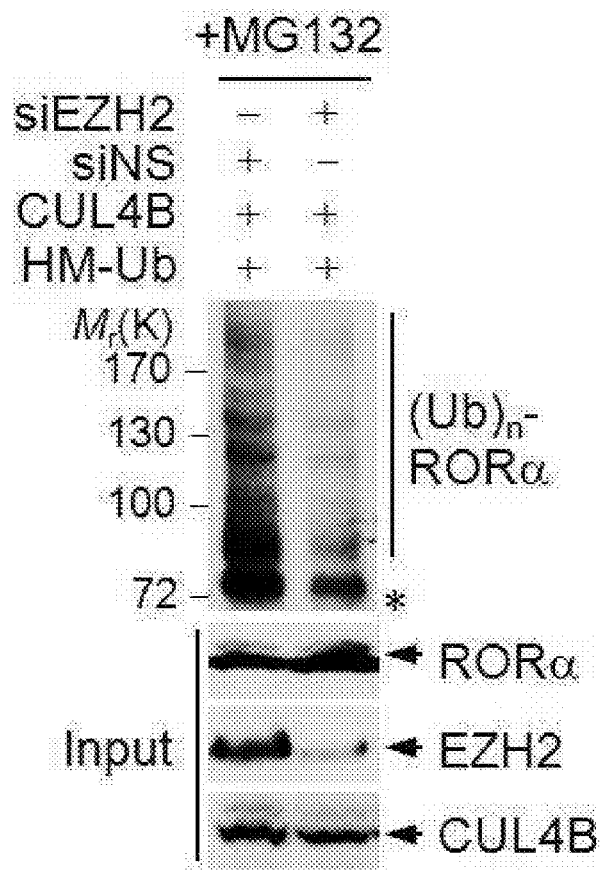
FIG. 34 shows that increased RORα ubiquitination by CUL4B was significantly decreased by knockdown of EZH2.

Since only CUL4A and CUL4B E3 ubiquitin ligases were reported to employ DDB1 as an adaptor, we examined the mutual binding of RORα to CUL4A and CUL4B. RORα bound to both CUL4A and CUL4B and introduction of EZH2 enhanced the binding as assessed by co-immunoprecipitation (FIG. 31). Based on the nuclear localization of CUL4B compared to the cytoplasmic localization of CUL4A, we tested one of the CUL4 paralogues, CUL4B, for RORα ubiquitination and protein stability assays. Knockdown of CUL4B significantly increased RORα protein levels (FIG. 32). To confirm whether CUL4B is responsible for RORα ubiquitination and EZH2-dependent RORα methylation, as a prerequisite for CUL4B-dependent ubiquitination, we introduced CUL4B and EZH2 shRNA and performed a RORα ubiquitination assay. Overexpression of CUL4B led to a marked increase in RORα ubiquitination (FIG. 33), and this increase was almost completely abolished by knockdown of EZH2 (FIG. 34). Taken together, our data strongly demonstrates that EZH2-mediated methylation of RORα triggers ubiquitination of RORα, and DCAF1 serves as a substrate receptor, along with DDB1, for the recognition of methylated RORα and its subsequent CUL4-dependent ubiquitination and degradation.

Example 13

Molecular Basis for the Recognition of Methylated Substrates by DCAF1

Figure 35:
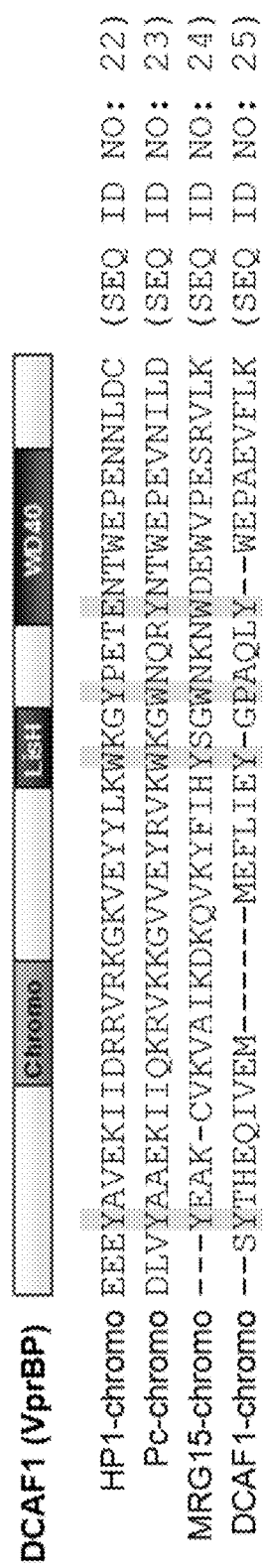
FIG. 35 shows sequences comparison between the chromo domains from HP1, Pc, MRG15, and the putative cDCAF1. Highly conserved aromatic residues are shaded.
Figure 36:
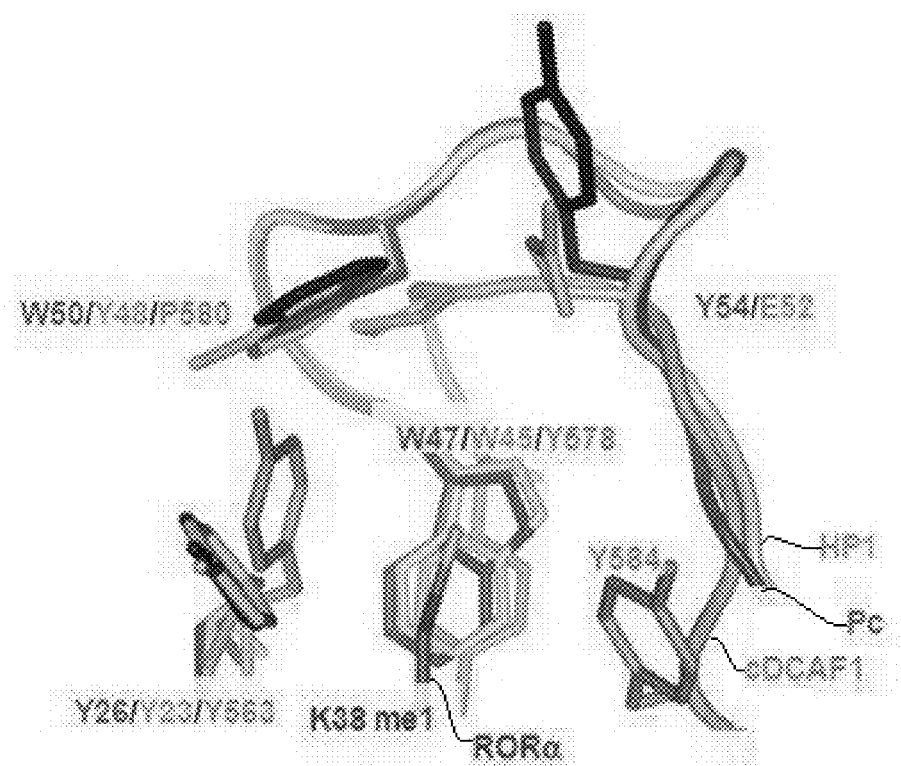
FIG. 36 shows that the model of cDCAF1 bound to RORα peptide is superimposed with the chromo domains of Pc and HP1. Four hydrophobic residues (Y563, Y578, P580 and Y584) in the cDCAF1 and overlapped residues in the other proteins are presented in the stick models and labelled. The methylated K38 of RORα peptide is also drawn in a stick model.
Figure 37:
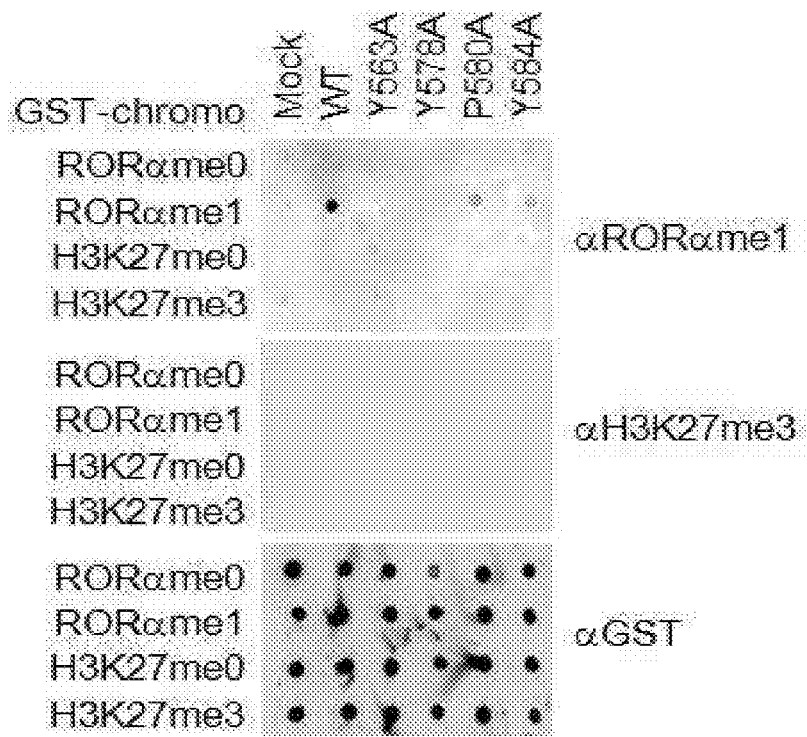
FIG. 37 shows that the binding of the GST-DCAF1 WT and chromo domain mutants (Y563A, Y578A, P580A, and Y584A) to the RORα K38me0, RORα K38me1, H3K27me0, and H3K27me3 peptides was determined by in vitro binding assay.
Figure 38:
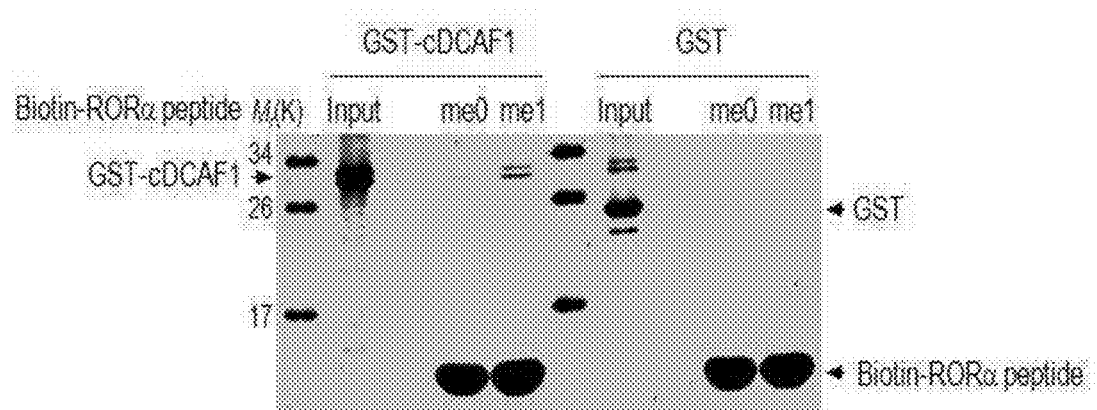
FIG. 38 shows that biotinylated RORα K38me0 and me1 peptides were immobilized onto streptavidin-conjugated Sepharose beads. GST and GST-DCAF1 chromo fusion proteins were added to the beads and the bound fraction was subjected to immunoblot analysis.

We then examined whether the putative chromo domain of DCAF1 (cDCAF1) could recognize a mono-methyl substrate. It has been reported that the hydrophobic amino acids within the binding pocket of the chromo domain are important for its function (i.e., the recognition of methylated substrates) (Fischle et al., 2003; Jacobs and Khorasanizadeh, 2002; Nielsen et al., 2002). Chromo domains of HP1, Pc, and MRG15 contain four hydrophobic amino acid residues within the binding pocket (FIG. 35) (Eissenberg and Elgin, 2000; Flanagan et al., 2005; Hayakawa et al., 2007; Jones et al., 2000; Lachner et al., 2001; Messmer et al., 1992; Pardo et al., 2002; Platero et al., 1995; Smothers and Henikoff, 2000). Based on the model structure of the cDCAF1 bound to RORα peptides, as well as the sequence alignment, Y563, Y578, P580, and Y584 amino acids of DCAF1 were proposed to be key residues forming a substrate recognition pocket that can fit into the methyl-amino group of K38 of the RORα peptide (FIG. 36). However, unlike the hydrophobic binding pockets of the chromo domain of Pc or HP1, which recognize trimethyl histone H3, DCAF1 possesses a smaller binding pocket, which cannot accommodate the trimethyl group of histone H3 (FIG. 36). These results allowed us to propose that DCAF1 functions as a putative mono-methyl reader. Therefore, in order to examine whether cDCAF1 directly recognizes the mono-methyl peptide, we performed an in vitro peptide binding assay of WT and mutant cDCAF1 with the peptides derived from non-methyl RORα, monomethyl RORα, non-methyl histone H3K27, and trimethyl histone H3K27. WT cDCAF1 could only bind to the mono-methyl RORα peptide, whereas the mutation of amino acid residues in the critical binding pocket of cDCAF1 (Y563A, Y578A, P580A, and Y584A) ablated the binding of cDCAF1 to the mono-methyl RORα peptide (FIG. 37). In parallel, a GST-pull-down assay confirmed that cDCAF1 selectively binds to mono-methyl RORα, but not non-methyl RORα (FIG. 38). Together, these in vitro binding assay results strongly suggest that cDCAF1 can specifically recognize mono-methyl RORα, but not trimethyl histone H3K27, by utilizing the hydrophobic binding pocket in the chromo domain. These results demonstrate that DCAF1 discerns only mono-methylation and specifically links methylation to ubiquitination-dependent degradation.

Figure 40:
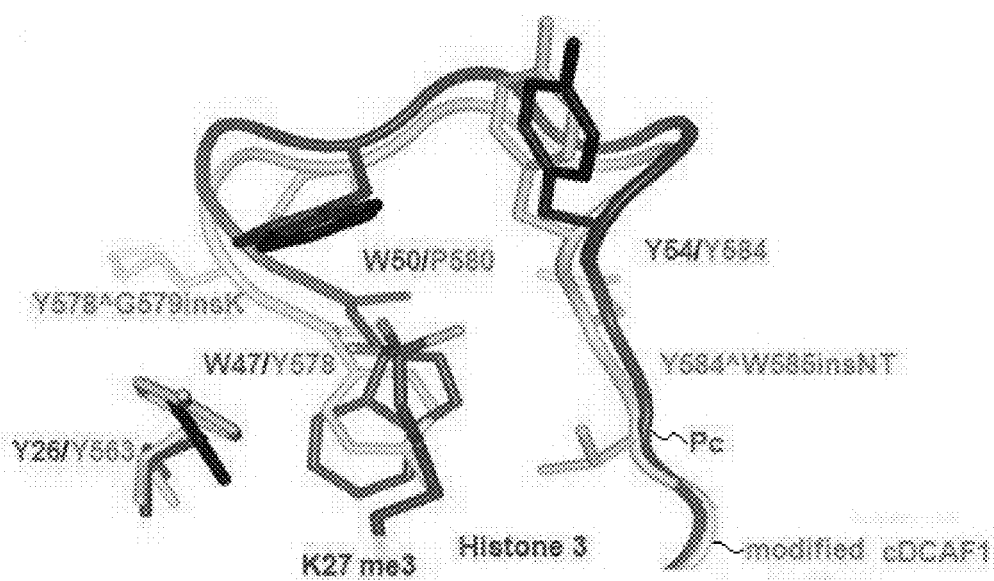
FIG. 40 shows that the modelled chromo domain of modified DCAF1 bound to the Lys trimethyl ammonium group is compared with the chromo domain of Pc. Y578^G579insK indicates a Lys residue inserted between Y578 and G579, and Y584^W585insNT represents an Asn and Thr residues inserted between Y584 and W585.
Figure 41:
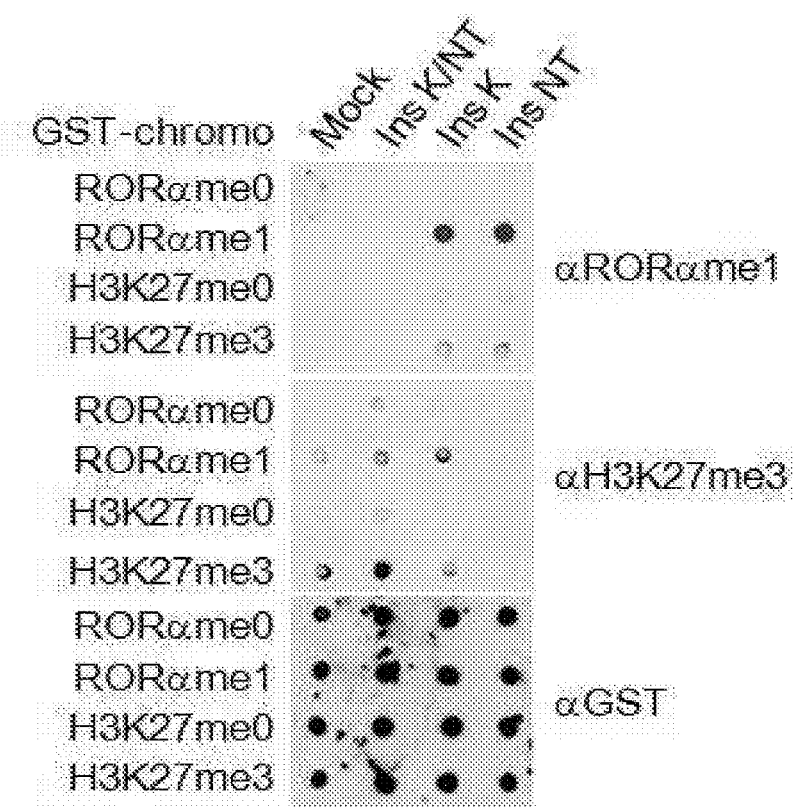
FIG. 41 shows that the binding of chromo domains of the K/NT-inserted, K-inserted, or NT-inserted mutants of DCAF1 with the RORα K38me0, RORα K38me1, H3K27me0, or H3K27me3 peptides was measured by in vitro binding assay.

To further clarify and confirm whether the ability of DCAF1 to read mono-methylation is due to its pocket size, we have explored a strategy to enlarge its pocket size, similar to that of Pc or HP1. From the sequence alignment and modeling analysis, it was predicted that the insertion of both Lys (K) (between Y578 and G579) and Asn-Thr (NT) residues (between Y584 and W585) could enlarge the pocket size (FIG. 39). Indeed, the insertion of both K and NT led to a decrease in the ability of DCAF1 to bind the mono-methyl RORα peptide, with an increase in the ability to recognize the trimethyl histone H3 peptide (FIGS. 40 and 41). On the other hand, the insertion of either K or NT did not affect the binding of DCAF1 to mono-methyl RORα peptides (FIG. 41). Based on in vitro peptide binding assay results, as well as modeling structures, we identified DCAF1 as the first mono-methyl reader, having a relatively small binding pocket that specifically accommodates mono-methyl substrates, but not di- or trimethyl substrates. Together, these results demonstrate that DCAF1 discerns mono-methylated substrates possessing a "Methyl Degron" and specifically functions to link mono-methylation to ubiquitin-dependent degradation machinery. Based on these findings, we suggest a previously unrecognized regulatory molecular mechanism where EZH2-DCAF1/DDB1/CUL4 serves as a novel methylation-specific E3 ubiquitin ligase complex that plays a crucial role in dynamic regulation of non-histone protein stability.

Example 14

Recognition of a "Methyl Degron" by DCAF1

Figure 42:
FIG. 42 shows a schematic representation of the RORα/H3 chimeric protein.
Figure 43:
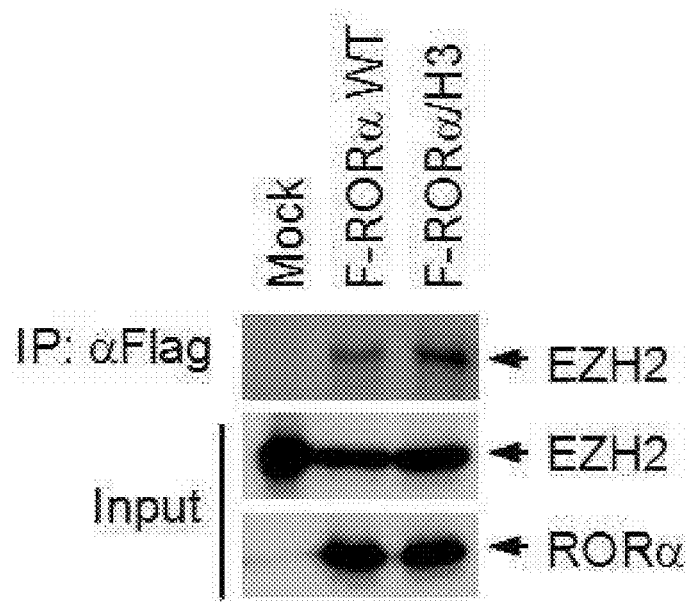
FIG. 43 and FIG. 44 show that cells were transfected with Flag-RORα WT or Flag-RORα/H3 chimeric mutant. Cell extracts were immunoprecipitated with anti-Flag antibody followed by immunoblot analysis against anti-EZH2 (FIG. 43) or anti-DCAF1 (FIG. 44) antibodies.
Figure 44:
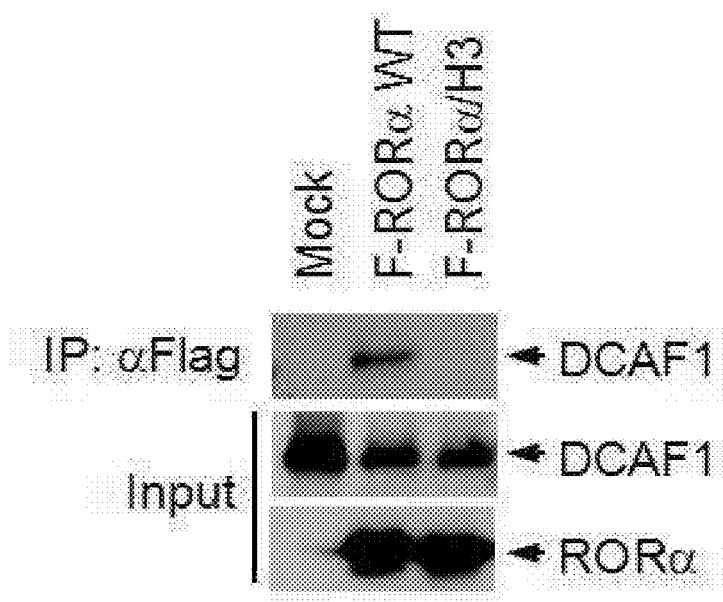
Figure 45:
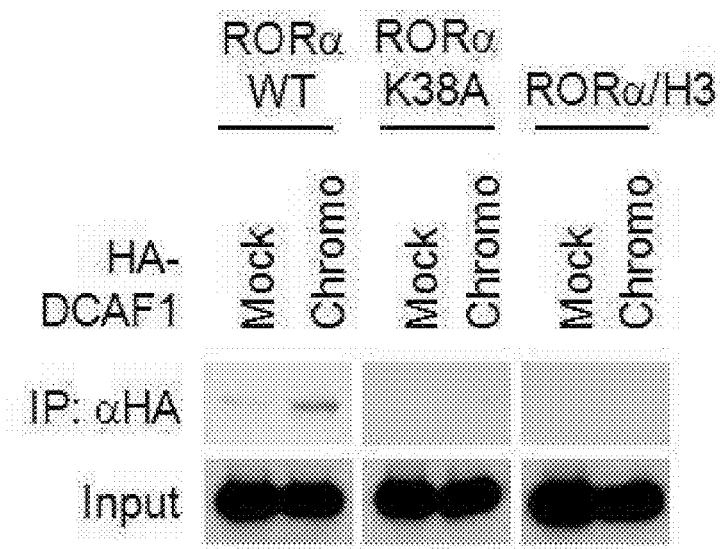
FIG. 45 shows that cells were transfected with RORα WT, RORα K38A, or RORα/H3 chimeric mutants in the absence or presence of the HA-DCAF1 chromo domain. An immunoprecipitation assay was performed with anti-HA antibody, and the bound RORα was detected by immunoblot analysis with anti-Flag antibody.

To test the possibility that a histone-like sequence within RORα acts as a molecular determinant required or even sufficient for recognition by DCAF1, we prompted to interchange the RORα histone-like sequence (amino acids 29-47) with that of the histone H3 sequence (amino acids 18-36) to generate a RORα/H3 chimeric protein (FIG. 42). Although the RORα/H3 chimeric protein bound to EZH2, as well as RORα WT (FIG. 43), it exhibited almost complete loss of binding ability to DCAF1, unlike RORα WT (FIG. 44). Furthermore, in contrast to RORα WT, neither RORα K38A nor the RORα/H3 chimeric protein exhibited comparable binding to the cDCAF1 (FIG. 45).

Figure 46:
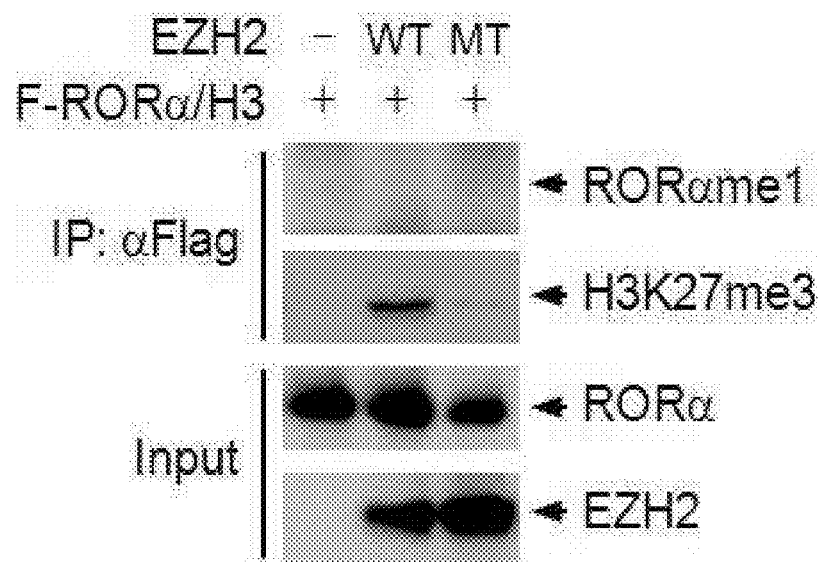
FIG. 46 shows that cells were transfected with either EZH2 WT or MT, and cell extracts were subjected to immunoprecipitation against anti-Flag antibody. Monomethyl RORα K38 levels and trimethyl H3K27 levels were detected with anti-RORαme1 antibody and anti-H3K27me3 antibody, respectively.
Figure 47:
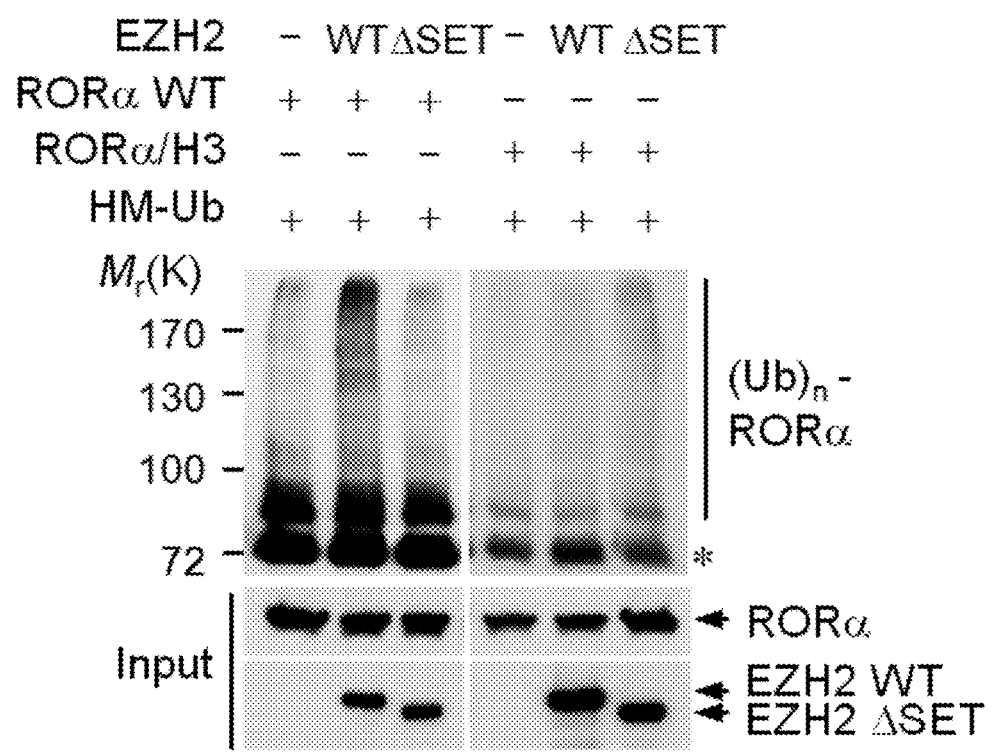
FIG. 47 shows that protein extracts from cells co-transfected with Flag-RORα or Flag-RORα/H3 chimeric mutants, EZH2 WT or ΔSET mutants, and HisMax-ubiquitin (HM-Ub) were subjected to pull-down with $Ni^{2+}$-NTA beads. Ubiquitination of RORα was assessed by anti-Flag antibody.

Because DCAF1 failed to interact with the RORα/H3 chimeric protein, we speculated that the RORα/H3 protein might be trimethylated by EZH2 similar to the histone H3K27, preventing it from being recognized by DCAF1 and subsequent ubiquitination-dependent degradation. Indeed, the RORα/H3 chimeric protein can be trimethylated by EZH2, as revealed by its detection by H3K27me3 antibodies, but not by RORαme1 antibodies (FIG. 46). Further, in contrast to RORα WT protein, the RORα/H3 chimeric protein failed to show an increase in ubiquitination upon the introduction of EZH2 WT (FIG. 47). Our results confirm that the replacement of the 19 amino acid histone-like sequence within RORα by the corresponding histone H3 sequences, is sufficient to restore trimethylation. Therefore, the ability of DCAF1 to specifically recognizing mono-methylated substrates and subsequently linking to the DDB1/CUL4B E3 ubiquitin ligase complex for degradation, is apparently conferred by the methylation status.

Figure 48:
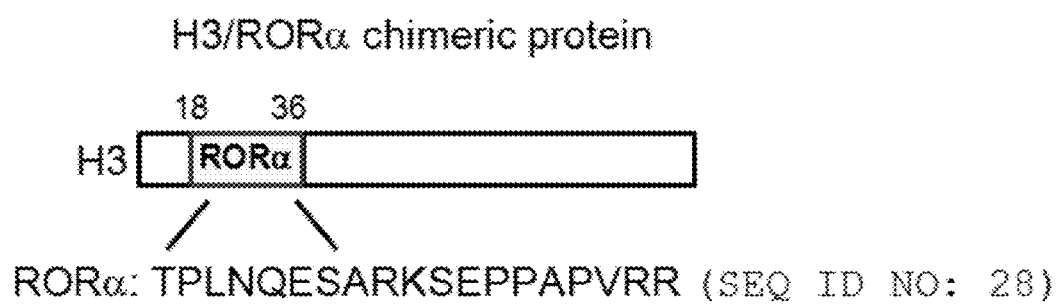
FIG. 48 shows a schematic representation of the H3/RORα chimeric protein.
Figure 49:
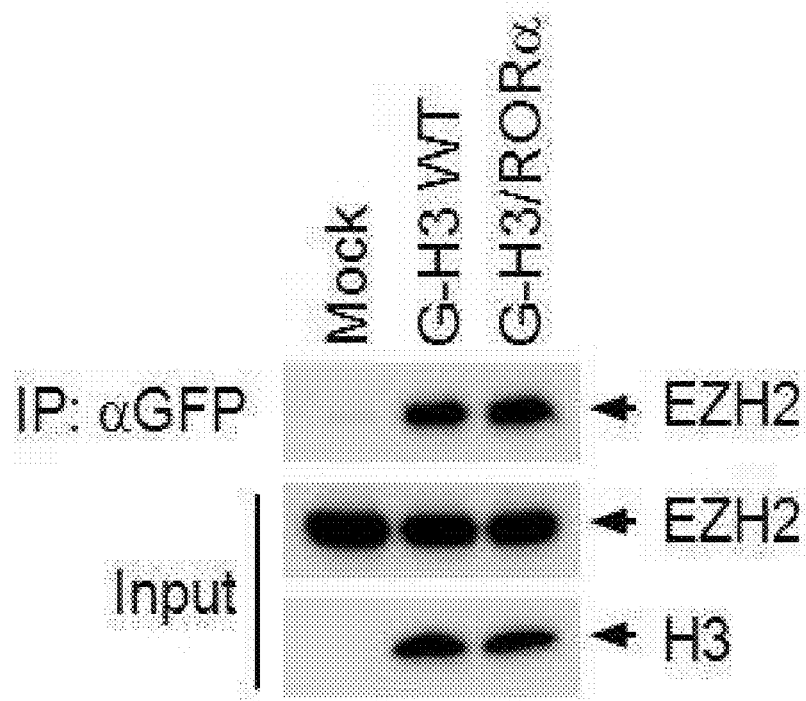
FIG. 49 and FIG. 50 show that cells were transfected with GFP-H3 WT or GFP-H3/RORα chimeric mutants. Cell extracts were immunoprecipitated with anti-GFP antibody followed by immunoblot analysis against anti-EZH2 (FIG. 49) or anti-DCAF1 (FIG. 50) antibodies.
Figure 50:
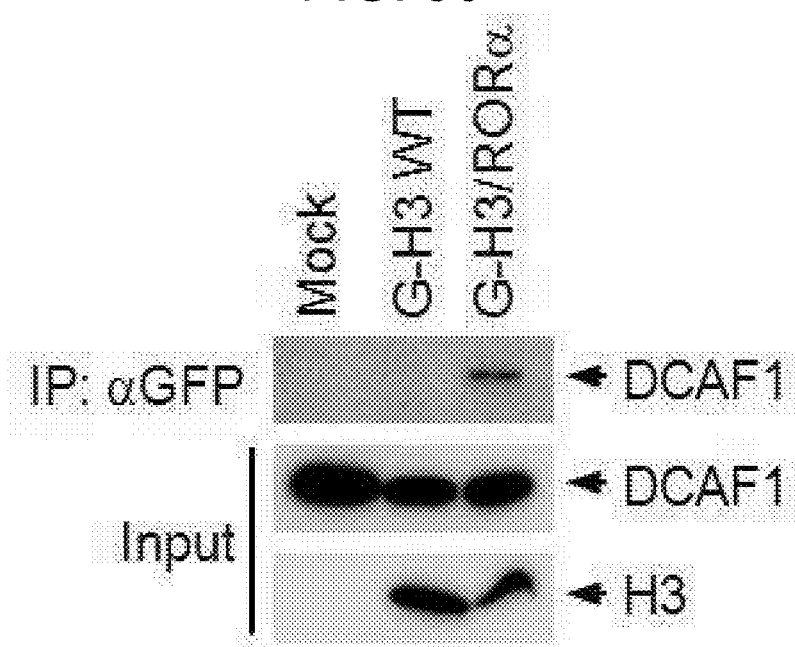
Figure 51:
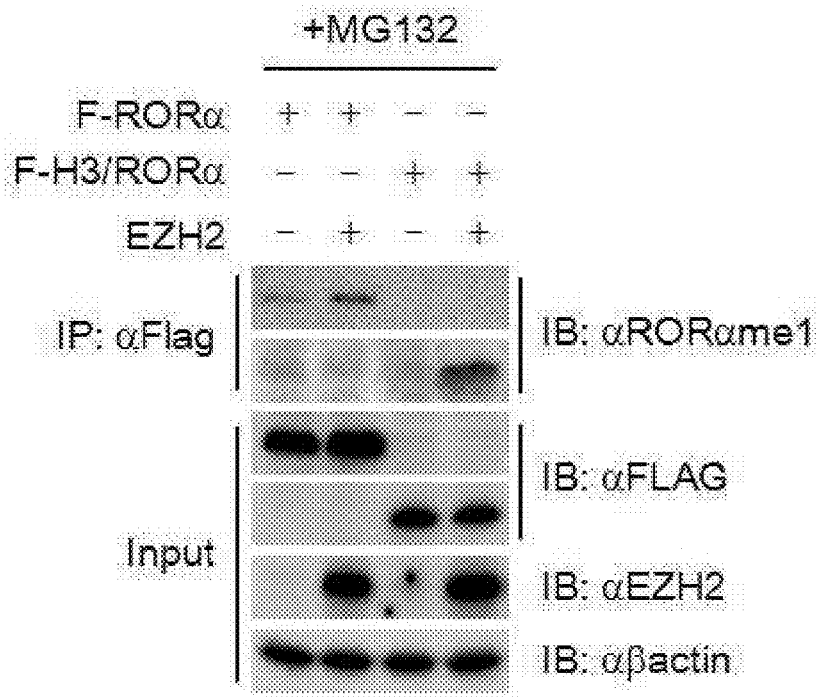
FIG. 51 shows that EZH2 overexpression led to increased mono-methylation of H3/RORα chimeric proteins.
Figure 52:
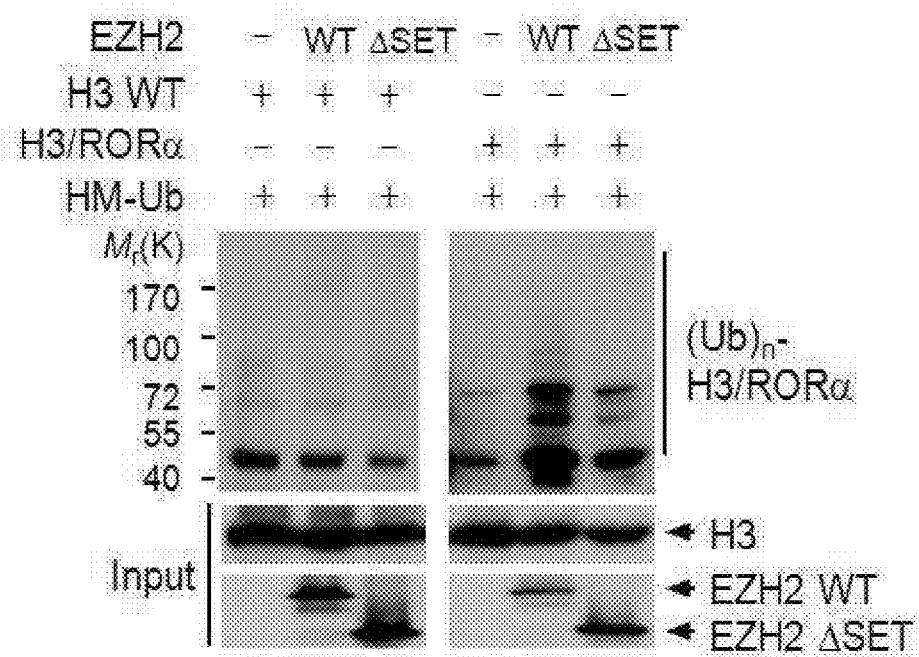
FIG. 52 shows that protein extracts from cells co-transfected with GFP-H3 WT or GFP-H3/RORα chimeric mutant, EZH2 WT or ΔSET mutant, and HisMax-ubiquitin (HM-Ub) were subjected to pull-down with $Ni^{2+}$-NTA beads. Ubiquitination of RORα was determined using anti-Flag antibody.

To further test the possibility that a histone-like sequence within RORα functions as a "Methyl-Degron" recognized by DCAF1 for subsequent ubiquitin-dependent degradation, we have inserted RORα histone-like sequence (amino acid 29-47) to the histone H3 sequence (-amino acid 18-36) to generate a H3/RORα chimeric protein (FIG. 48). The H3/RORα chimeric protein was able to interact with EZH2 in a similar fashion to histone H3 (FIG. 49), but intriguingly, it acquired binding ability to DCAF1 unlike histone H3 (FIG. 50). Indeed, the H3/RORα chimeric protein can be mono-methylated by EZH2, as revealed by its detection with RORαme1 antibodies, similar to RORα WT (FIG. 51). Furthermore, unlike histone H3 proteins, the H3/RORα chimeric protein showed increased ubiquitination in an EZH2 activity-dependent manner (FIG. 52). An EZH2ΔSET mutant, that is deficient in enzymatic activity, significantly attenuated ubiquitination of the H3/RORα chimeric protein. Together, these data confirm that the histone-like sequence within RORα functions as a "Methyl-Degron" which is subject to DCAF1 binding and subsequent ubiquitin-dependent degradation.

Example 15

Figure 53:
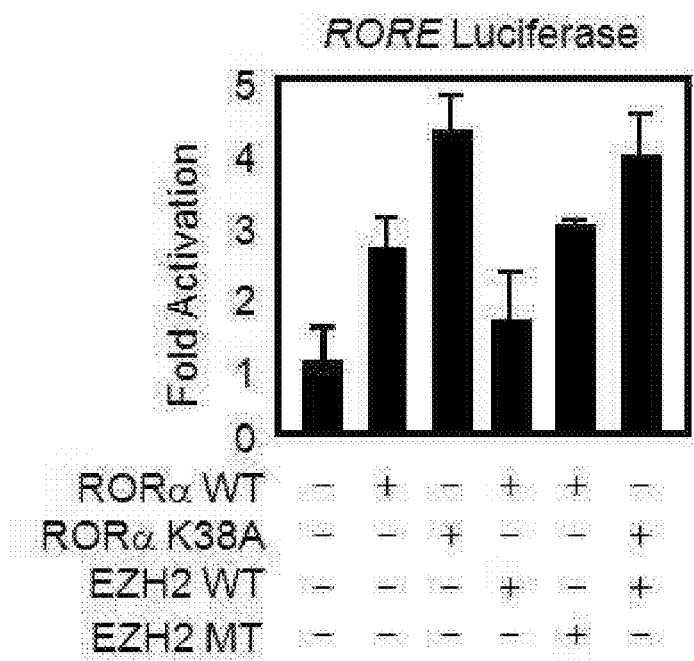
FIG. 53 to FIG. 55 show 5× RORE-luciferase reporter plasmid transfected into 293T cells with the indicated plasmids. Luciferase activity was measured at 48 h after transfection and normalized by β-galactosidase activity. Values are expressed as mean±SD for three independent experiments. MG132 (20 μM) was treated for 24 h.
Figure 54:
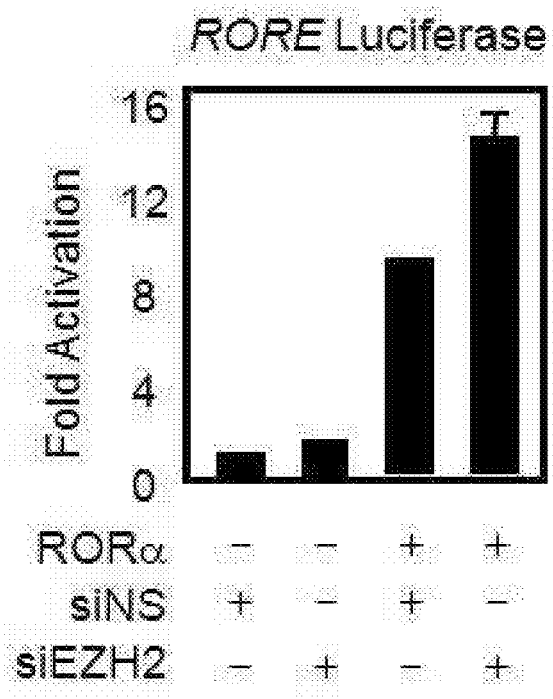
Figure 55:
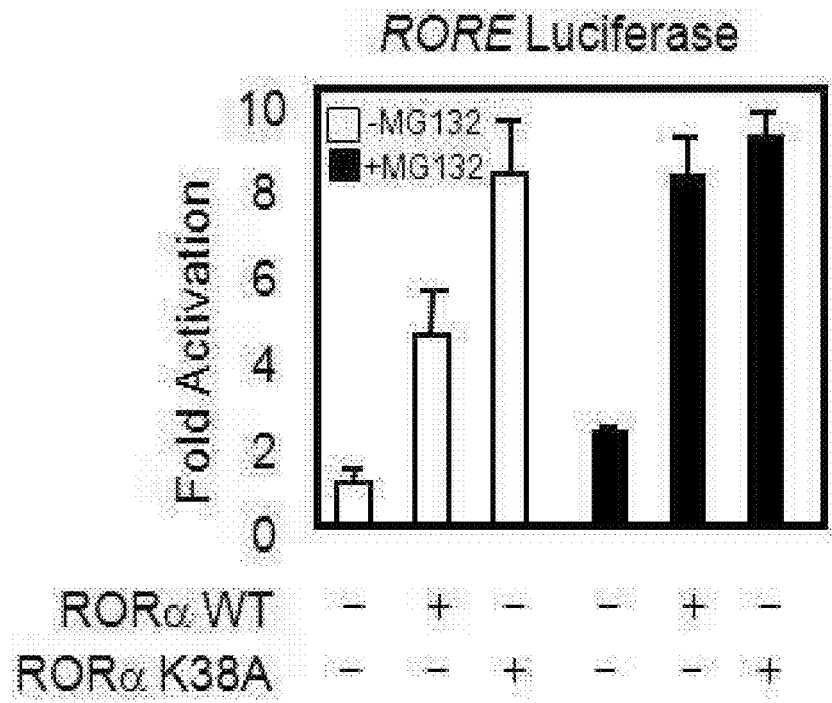
Figure 56:
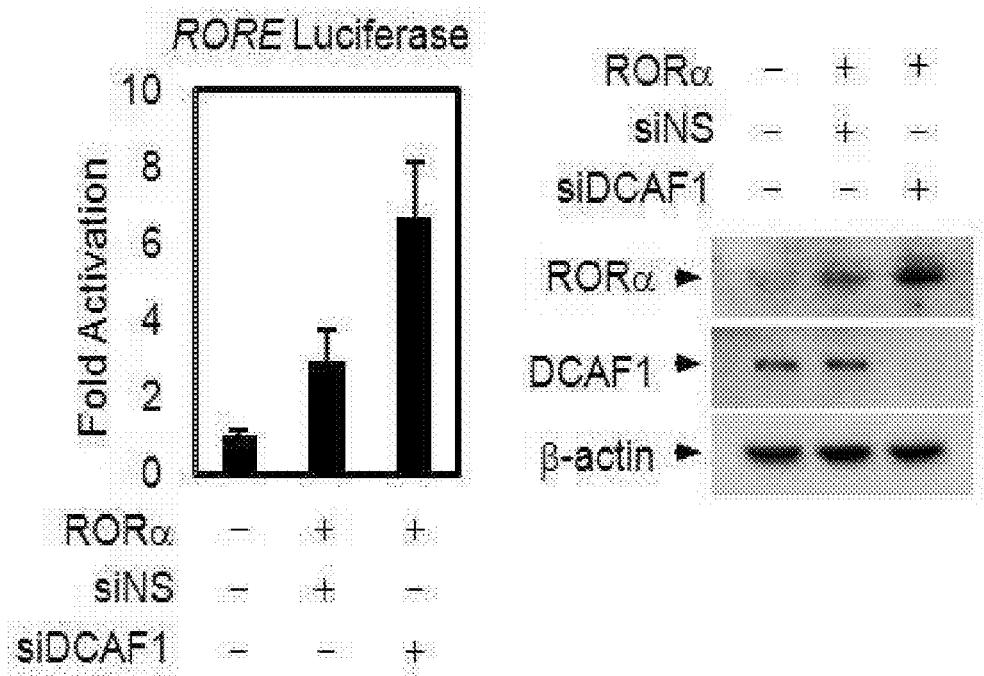
FIG. 56 shows 5× RORE-luciferase reporter plasmid transfected into 293T cells with RORα and siRNA for DCAF1. Immunoblot analysis was performed to detect RORα and DCAF1 protein levels. Values are expressed as mean±SD for three independent experiments.

Methylation-Dependent Ubiquitination of RORα Leads to the Transcriptional Repression of RORα Target Genes Next, we examined the functional consequence of EZH2-dependent methylation and subsequent ubiquitin-dependent degradation of RORα on the transcription of RORα-dependent target genes. Introduction of EZH2 WT, but not EZH2 MT, attenuated RORα-dependent activation of RORE-luciferase activity (FIG. 53). Compared to RORα WT, RORα K38A was able to further increase RORE-luciferase activity (FIG. 53). Similarly, EZH2 knockdown resulted in potentiating the transcriptional activity of RORα (FIG. 54). Intriguingly, the RORα K38A mutant showed more potent transcriptional activity compared to RORα WT in the absence of MG132, whereas in the presence of MG132, this difference was abolished (FIG. 55). In accordance with the ubiquitination assay data FIG. 28 DCAF1 knockdown led to increased transcriptional activity of RORα (FIG. 56). In parallel, immunoblot analysis confirmed that the increased RORE-luciferase activity is correlated with the increased RORα protein levels (FIG. 56). These data indicate that EZH2-dependent methylation and DCAF1-mediated, ubiquitin-dependent degradation of RORα affects the transcription of RORα-dependent target genes.

Figure 57:
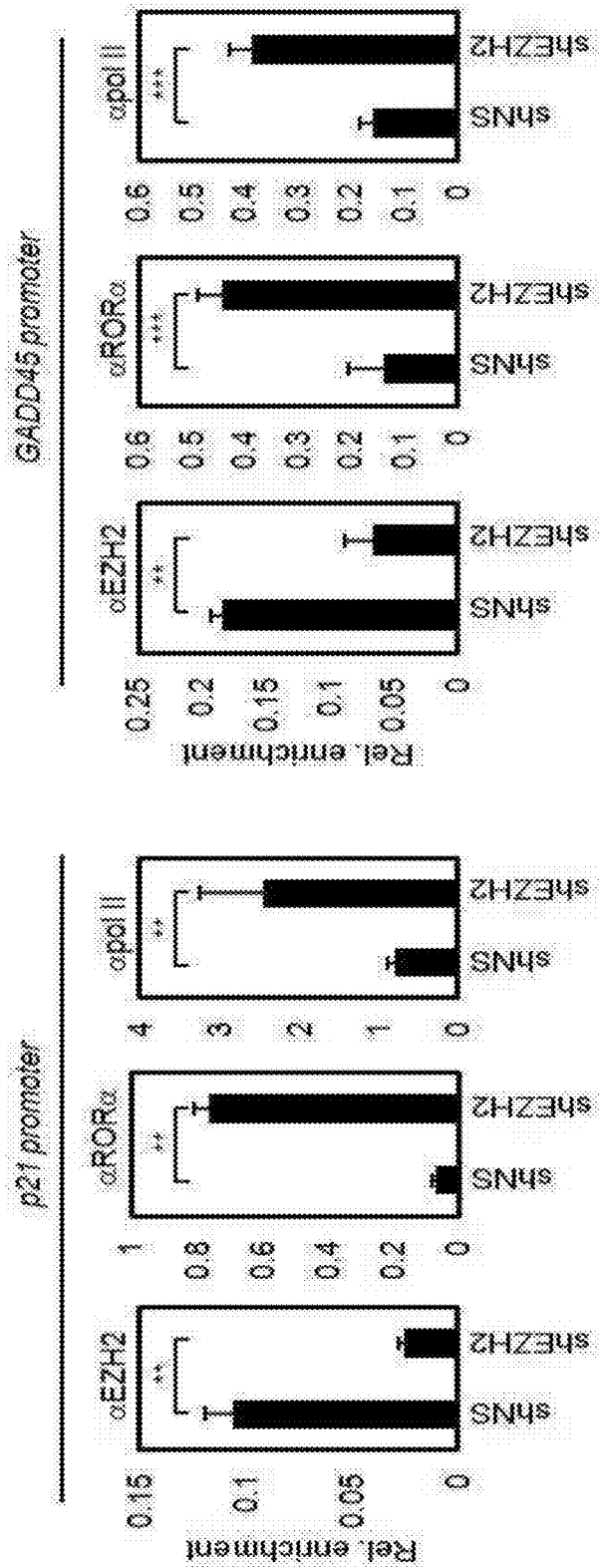
FIG. 57 shows ChIP assays performed on the p21 or GADD45 promoters in the presence of control shRNA or EZH2 shRNA in MCF7 cells.

With p21 as one of the well-known RORα target genes with a functional RORE on the promoter (Grechez-Cassiau et al., 2008; Steinman et al., 1998), and in an effort to examine whether p21 transcription levels are affected by EZH2, we performed ChIP assays on a p21 promoter in MCF7 breast cancer cells. The ChIP assay further confirmed that EZH2 knockdown increased RORα recruitment concomitant with increased RNA polymerase II recruitment (FIG. 57). A GADD45 promoter containing RORE was also examined, and similar results were observed (FIG. 57). Together, these data indicate that EZH2-dependent methylation triggers ubiquitin-dependent degradation of RORα, leading to transcriptional repression of RORα target genes.

Example 16

Functional Consequence of Methylation-Dependent RORα Ubiquitination

Figure 58:
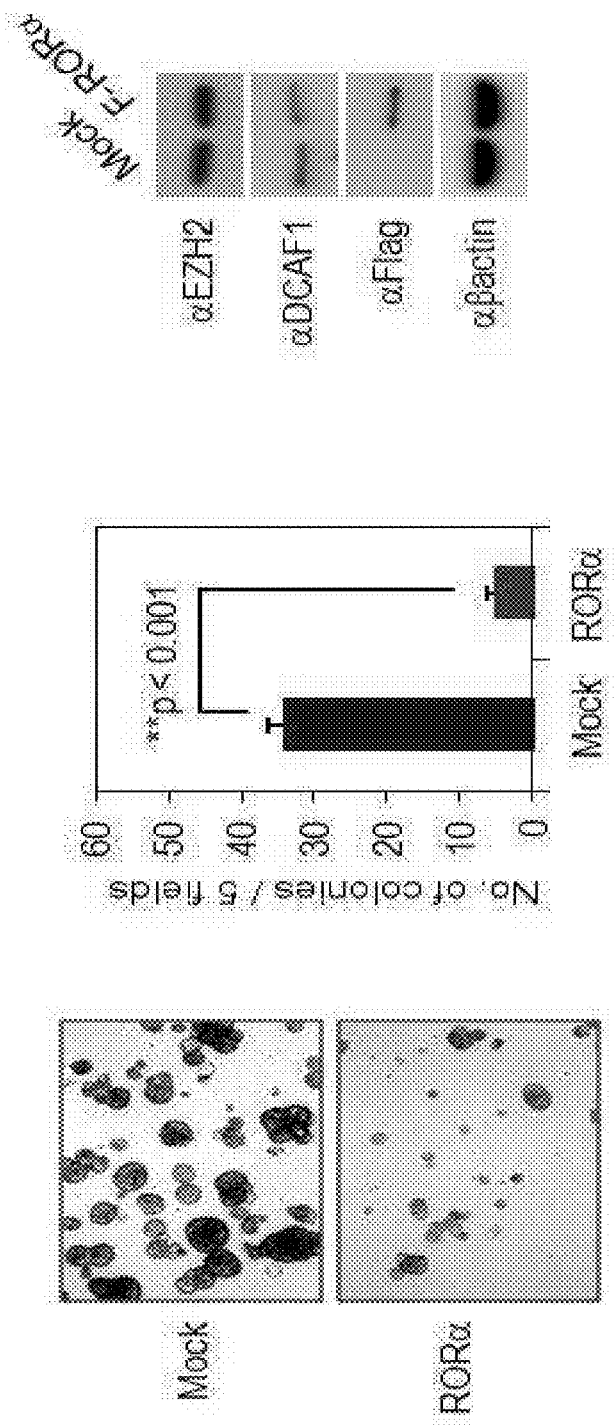
FIG. 58 to FIG. 60 show anchorage-independent growth of MCF7 breast cancer cells stably expressing empty vector or RORα (FIG. 58), or transfected with control siRNA or DCAF1 siRNA (FIG. 59), and cells treated with vehicle or DZNep (2 μM) (FIG. 60), in soft agar. Representative images are shown for each group. Immunoblot analysis was performed to detect each protein level.
Figure 59:
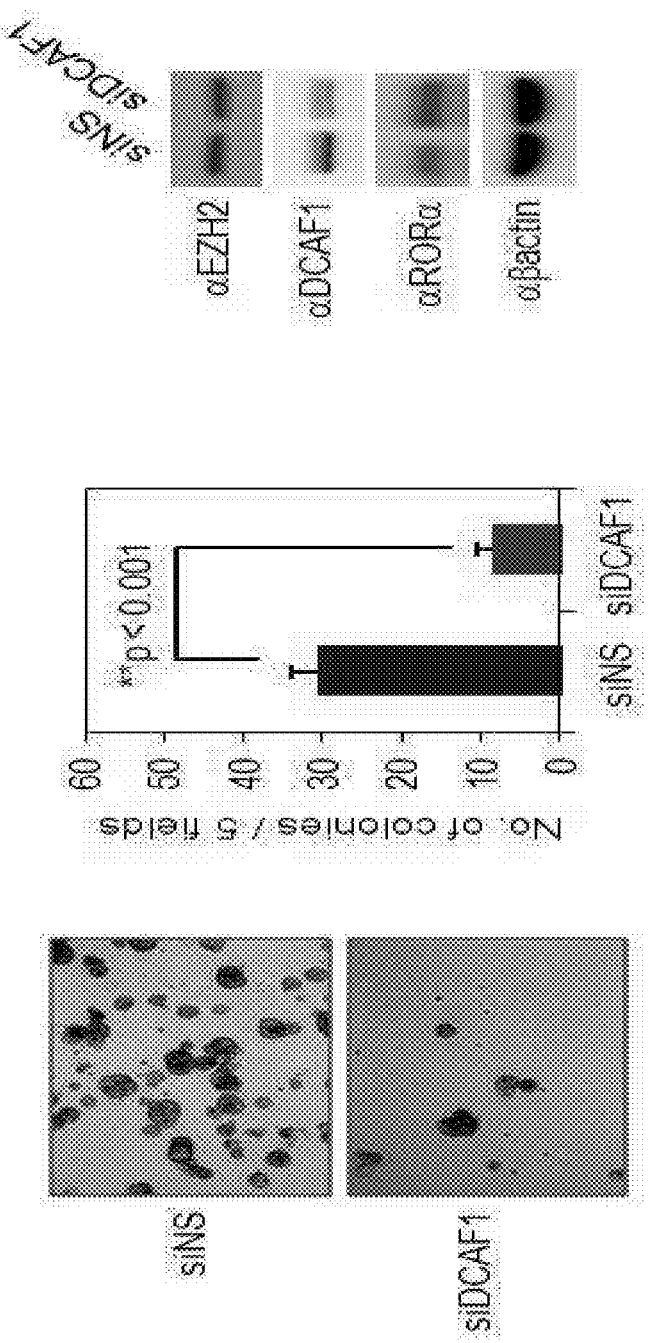
Figure 60:
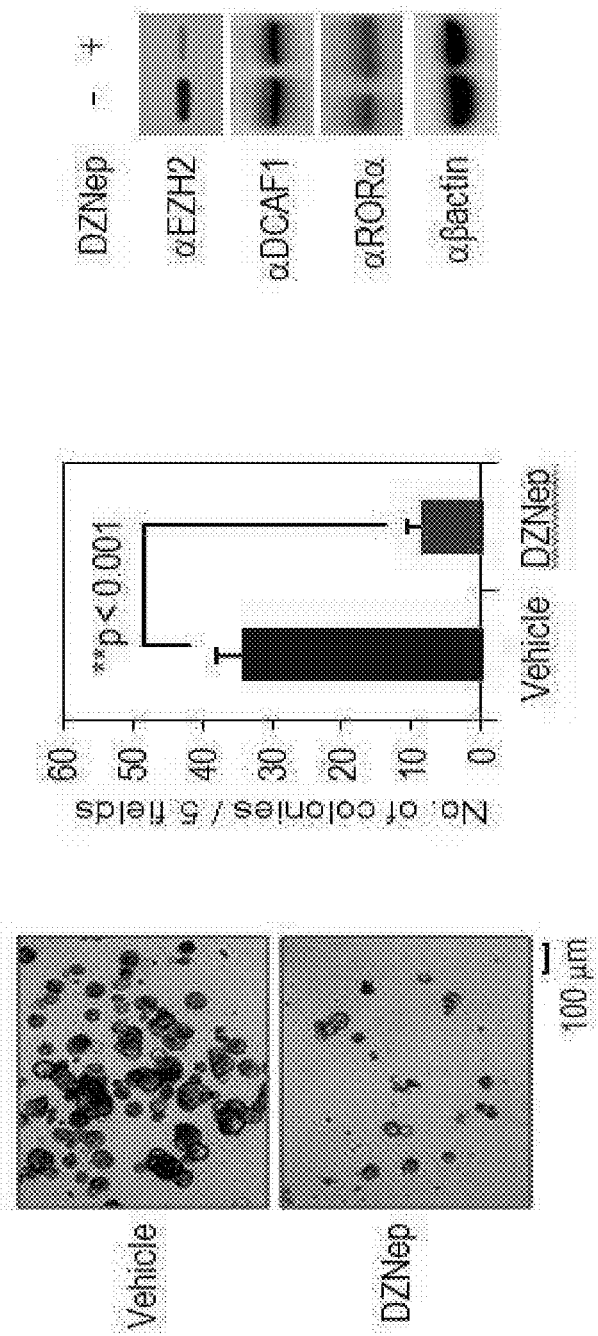

Given that DCAF1 is responsible for RORα degradation, it is reasonable to expect that there must be a physiologically relevant function that underlies these intriguing findings. In breast and prostate cancers, elevated EZH2 protein levels have been observed, suggesting that EZH2 may be acting as an oncogene, and therefore might be used as a marker for cancer diagnosis (Bachmann et al., 2006; Kleer et al., 2003; Varambally et al., 2002). In order to determine whether RORα protein levels ultimately alter the cell's ability to transform, we have taken several approaches in regulating RORα protein levels. First, overexpression of RORα in MCF7 breast cancer cells led to a significant reduction in colonies, compared to vector control in soft agar (FIG. 58). Second, the knockdown of DCAF1 also led to a marked reduction in the number of colonies in soft agar by stabilizing RORα protein levels (FIG. 59). Moreover, MCF7 breast cancer cells treated with DZNep (1 μM) also had an inhibitory effect on cellular transformation (FIG. 60). Together, these transformation assay results strongly support our inverse correlation between EZH2 and RORα protein levels conferred by methylation-dependent ubiquitination of RORα.

Figure 61:
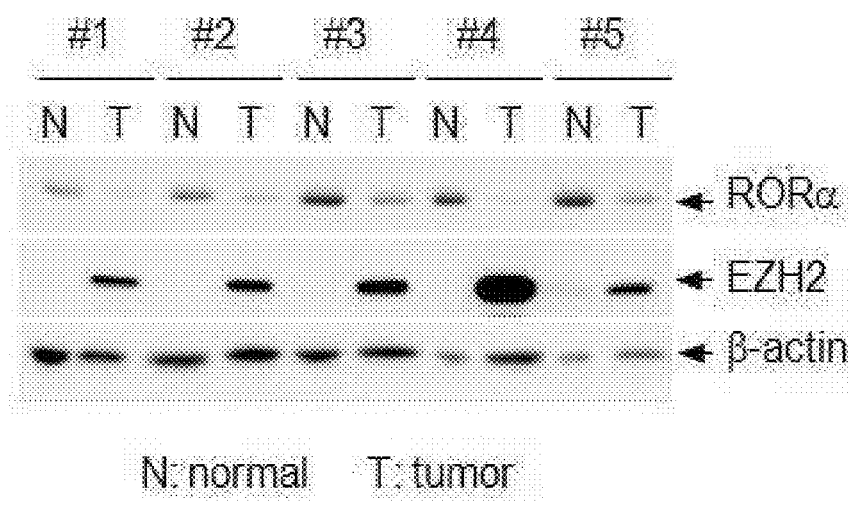
FIG. 61 shows the immunoblot analysis of RORα and EZH2 in human breast tumor tissue samples (T) along with matched normal tissue samples (N).
Figure 62:
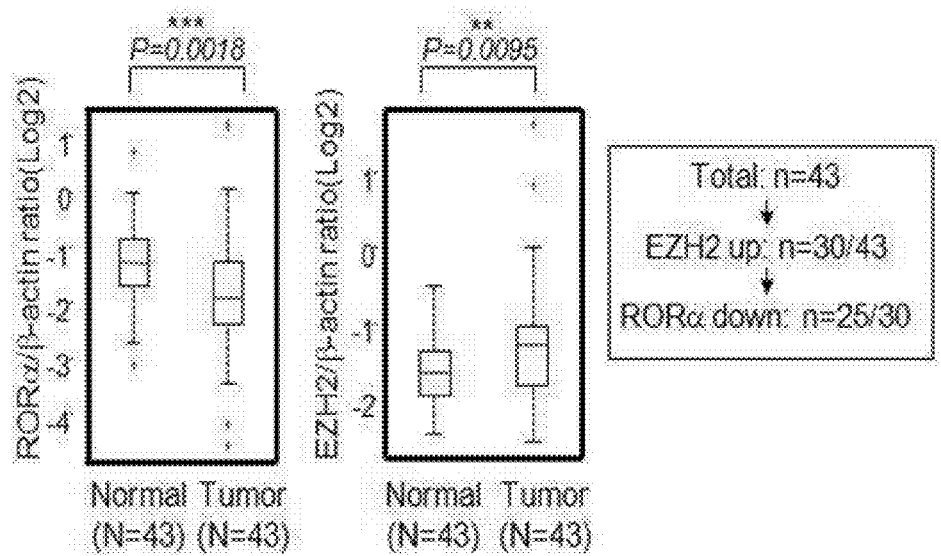
FIG. 62 shows the statistical analysis of the ratio of RORα or EZH2 to β-actin in 43 human breast tumor samples compared to matched normal counterparts calculated by paired students' t-test. Data are presented as whisker graphs, showing the median and the distribution of 50% (bar) and 99.3% (whisker) of all specimens examined.  $p<0.05$ and * $p<0.005$. Shown is a summary of protein expression analysis from human breast tumor specimens.
Figure 63:
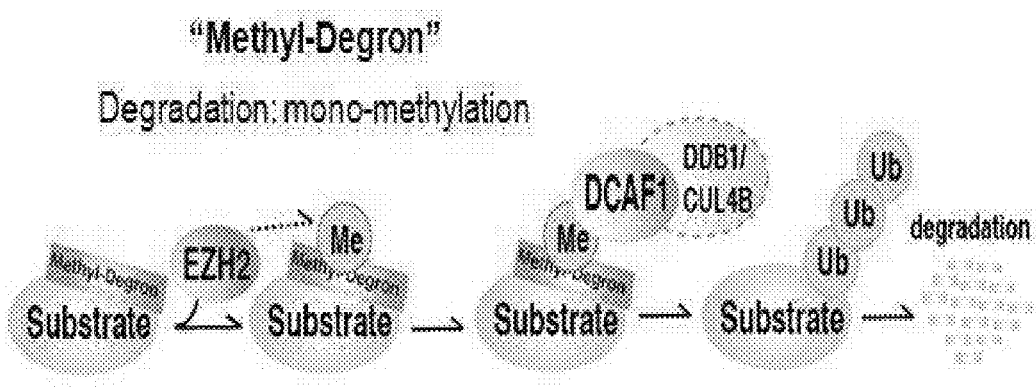
FIG. 63 shows the proposed model of DCAF1 serving as a methyl reader that specifically recognizes "Methyl-Degron", thereby allowing DDB1/CUL4-dependent ubiquitination and subsequent degradation of RORα by the 26S proteasome.

The inverse correlation between EZH2 and RORα was found in breast tumor tissue specimens compared to normal counterparts. RORα protein levels were very low in tumors exhibiting high levels of EZH2 levels (FIG. 61), strongly supporting the biological importance of these findings. Indeed, reduced RORα and elevated EZH2 protein levels in the tumor samples compared to normal samples were statistically significant (FIG. 62). Of 43 breast cancer patient specimens, there were 30 cases where EZH2 protein levels were higher in the tumor samples compared to normal samples. Within these 30 cases, 25 tumor specimens showed markedly reduced RORα protein levels, supporting the idea that elevated levels of EZH2 in the tumors might facilitate RORα degradation.

What is claimed is:

1. A method of regulating protein lifespan, comprising utilizing a protein fused with methyl degron peptide.

* * * * *